US012310944B2

(12) United States Patent
Sun et al.

(10) Patent No.: US 12,310,944 B2
(45) Date of Patent: May 27, 2025

(54) SELECTIVE BUTYRYLCHOLINESTERASE INHIBITOR OR PHARMACEUTICALLY ACCEPTABLE SALT THEREOF, PREPARATION METHOD AND USE THEREOF

(71) Applicant: CHINA PHARMACEUTICAL UNIVERSITY, Nanjing (CN)

(72) Inventors: Haopeng Sun, Nanjing (CN); Hongyu Yang, Nanjing (CN); Tingkai Chen, Nanjing (CN); Yao Chen, Nanjing (CN); Feng Feng, Nanjing (CN); Chenxi Du, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 30 days.

(21) Appl. No.: 16/967,401

(22) PCT Filed: Sep. 16, 2019

(86) PCT No.: PCT/CN2019/105879
§ 371 (c)(1),
(2) Date: Aug. 4, 2020

(87) PCT Pub. No.: WO2021/042410
PCT Pub. Date: Mar. 11, 2021

(65) Prior Publication Data
US 2023/0165833 A1 Jun. 1, 2023

(30) Foreign Application Priority Data

Sep. 5, 2019 (CN) .......................... 201910841091.4

(51) Int. Cl.
| | |
|---|---|
| A61K 31/381 | (2006.01) |
| A61K 31/167 | (2006.01) |
| A61K 31/195 | (2006.01) |
| A61K 31/24 | (2006.01) |
| A61K 31/277 | (2006.01) |
| A61K 31/341 | (2006.01) |
| A61K 31/40 | (2006.01) |
| A61K 31/4164 | (2006.01) |
| A61K 31/426 | (2006.01) |
| A61K 31/4402 | (2006.01) |
| A61P 25/28 | (2006.01) |

(52) U.S. Cl.
CPC .......... *A61K 31/381* (2013.01); *A61K 31/167* (2013.01); *A61K 31/195* (2013.01); *A61K 31/24* (2013.01); *A61K 31/277* (2013.01); *A61K 31/341* (2013.01); *A61K 31/40* (2013.01); *A61K 31/4164* (2013.01); *A61K 31/426* (2013.01); *A61K 31/4402* (2013.01); *A61P 25/28* (2018.01)

(58) Field of Classification Search
None
See application file for complete search history.

(56) References Cited

FOREIGN PATENT DOCUMENTS

| | | | |
|---|---|---|---|
| JP | 2013018729 A | * 1/2013 | |
| WO | WO-0058270 A2 | * 10/2000 | ............. A61K 31/52 |

OTHER PUBLICATIONS

American Chemical Society. Chemical Abstract Service. RN 298683-16-6, Entered into STN: Oct. 24, 2000 (Year: 2000).*
American Chemical Society. Chemical Abstract Service. RN 1296484-21-3, Entered into STN: May 18, 2011 (Year: 2011).*
American Chemical Society. Chemical Abstract Service. RN 1030774-88-9, Entered into STN: Jul. 28, 2004 (Year: 2004).*
American Chemical Society. Chemical Abstract Service. RN 1389475-01-7, Entered into STN: Aug. 12, 2012 (Year: 2012).*

* cited by examiner

*Primary Examiner* — Brandon J Fetterolf
*Assistant Examiner* — Gillian A Hutter
(74) *Attorney, Agent, or Firm* — CBM PATENT CONSULTING, LLC

(57) ABSTRACT

The present invention discloses a selective butyrylcholinesterase inhibitor having a general formula (I) or a pharmaceutically acceptable salt thereof, a preparation method and use thereof. The treatment efficacy of Alzheimer's disease, especially moderate to severe Alzheimer's disease, is tested through butyrylcholinesterase inhibitory activity, selectivity screening and toxicity to nerve cells as a carrier, and it is found that it has good target activity in vitro, extremely high selectivity and drug safety, can be used as a lead substance for further development of the treatment of Alzheimer's disease by selectively inhibiting butyrylcholinesterase.

6 Claims, No Drawings

SELECTIVE BUTYRYLCHOLINESTERASE INHIBITOR OR PHARMACEUTICALLY ACCEPTABLE SALT THEREOF, PREPARATION METHOD AND USE THEREOF

TECHNICAL FIELD

The present invention relates to a cholinesterase inhibitor or a pharmaceutically acceptable salt thereof, a preparation method and use thereof, and in particular to a selective butyrylcholinesterase inhibitor or a pharmaceutically acceptable salt thereof, a preparation method and use thereof.

BACKGROUND ART

Alzheimer's Disease (AD) is a kind of central neurodegenerative disease, and the patient's brain tissue shows imperceptible tiny changes which can generate obvious symptoms after long-term accumulation in the body, such as memory loss, language barrier, etc. In the long run, the deterioration of various disorders will interfere with the cognition and behavior, and even lead to personality changes in the patient. Currently, as the aging of the population has become a global problem, AD has become a great threat to the health of the elderly as well as to the medical resources of the society as a whole. According to World Alzheimer Reports 2006, 47 million people worldwide have dementia, and this figure is expected to rise to one hundred million by 2050. In the population over 60 years old in China, the incidence of AD has reached as high as 1.9%, which not only imposes a great burden on families and social economy, but also has become the fourth leading cause of death in the elderly following heart disease, tumors, and cerebrovascular disease. At present, no method for radically treating AD exists, and the existing medicines cannot repair nerves damaged irreversibly and only can delay the disease process of AD. Therefore, the search for effective drugs for treating AD has become a critical and instant problem in the medical field. Currently, five anti-AD drugs approved by FDA are all ChEI: tacrine, donepezil, galanthamine and rivastigmine, except for memantine, which is an N-methyl-D-aspartic acid receptor (NMDAR) antagonist. At present, ChEI is still the first line drug for the treatment of AD. However, these drugs have a certain therapeutic effect on mild AD in the early and middle stages, and effective drugs for treating severe AD are still lacking to date.

Although the discovery of AD has been over a century, the exact etiology of AD has not been concluded so far since it is a very complex neurodegenerative syndrome of the brain. Currently available studies indicate that the neuropathological features of AD are mainly: neuronal loss, reduction of neurotransmitter levels, formation of senile plaques (SP), and neurofibrillary tangles (NFT). Among them, the reduction of neurotransmitter levels is mainly indicated by the massive deletion of acetylcholine (ACh) in brain; SP is formed primarily by amyloid β (Aβ) deposition; and NFT is caused by hyperphosphorylation of Tau protein. Scientists have long sought to find the etiology and treatment strategy for AD through intensive studies of the above-mentioned conditions. The well-known Cholinergic Hypothesis has been proposed for neuronal loss and reduction of neurotransmitter levels; an Amyloid Hypothesis has been proposed for the Aβ deposition; and the hyperphosphorylation of Tau protein has been considered to be caused by the defects in activity of phosphoesterase which promotes dephosphorylation of Tau protein and excessive involvement of protein kinase which participates in phosphorylation of Tau protein. In addition, inflammatory reactions that cause changes in the internal environment of the brain's body fluids, elevated levels of reactive oxygen radicals, and disturbances in immune regulation in the brain are also considered as potential causes.

Of these etiologies, the Cholinergic Hypothesis is currently well recognized, which provides the first rational approach to the treatment of AD. According to the Cholinergic Hypothesis, in the pathological process of AD, a large number of cholinergic neurons is lost in forebrain and basal nucleus of a patient, cholinergic receptors and post-receptor signal transduction are damaged, such that the ACh level in the projection area of nerve fibers, namely hippocampus and cerebral cortex, is obviously reduced. ACh presents in the central nervous system as an important neurotransmitter, and functions as improving memory and promoting learning. The cognitive decline in AD patients is significantly correlated with the reduction in ACh levels in these areas, and the cognitive ability of humans and animals can be affected by cholinergic drugs. Thus, the symptoms of AD can be alleviated by restoring ACh levels through improving the cholinergic system. There are two kinds of cholinesterase responsible for the hydrolysis of ACh in the brain, one being acetylcholinesterase (AChE), also known as true cholinesterase, the other being butyrylcholinesterase (BuChE), also known as pseudocholinesterase. AChE is mainly expressed by neurons, while BuChE activity is mainly associated with neuritic plaques, neurofibrillary tangles and glial cells in AD patients. In healthy brain, AChE activity dominates (80%), while BuChE appears to only play a supporting role. However, in progressive AD, the levels of AChE in the brain gradually decrease to 55-67% of normal level, while the levels of BuChE increase to 120% of normal level. This suggests that in late AD, BuChE replaces the dominating role of AChE, becoming the main metabolic enzyme for hydrolyzing ACh. Thus, BuChE is more of a concern in severe AD. It has been reported that both classical selective AChE inhibitors and non-selective cholinesterase inhibitors have some degree of peripheral cholinergic side effects due to the lack of strong tissue selectivity, which is not observed with selective BuChE inhibitors. This indicates that selective BuChE inhibitors have greater drug safety in treating AD.

In conclusion, the design of the high-selectivity BuChE inhibitor has the advantages of safety, high efficiency, stability, reasonability and the like for treating AD, and is considered as an exact effective means for treating AD. However, most of the existing BuChE inhibitors have the defects of small quantity, lack of specificity due to wide biological activity, lack of structural novelty and diversity, poor bioavailability and the like. Therefore, the development of the high-selectivity BuChE inhibitor with a brand-new backbone has great significance and value.

SUMMARY OF THE INVENTION

The objective of the present invention: The objective of the present invention is to provide a selective butyrylcholinesterase inhibitor or a pharmaceutically acceptable salt thereof, which has strong biological activity, high safety and high bioavailability.

Another objective of the present invention is to provide a method for preparing the selective butyrylcholinesterase inhibitor or a pharmaceutically acceptable salt thereof.

A final objective of the present invention is to provide use of the selective butyrylcholinesterase inhibitor or a pharmaceutically acceptable salt thereof.

The technical solution: The present invention provides a selective butyrylcholinesterase inhibitor having a general formula (I) or a pharmaceutically acceptable salt thereof,

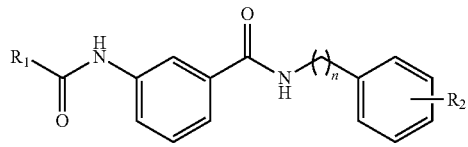
(I)

wherein n is an integer from 0 to 3;
$R_1$ represents

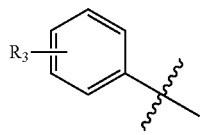

or thiophene, furan, pyrrole, pyridine, thiazole, imidazole or cyclohexane substituted with $R_4$;
  wherein $R_3$ represents hydroxyl, $C_1$-$C_4$ carboxyl, $C_1$-$C_4$ aldehyde group, halogen, $C_1$-$C_4$ alkyl, $C_1$-$C_4$ alkyl substituted with halogen, $C_1$-$C_4$ alkoxy, $C_1$-$C_4$ alkoxycarbonyl, $C_1$-$C_4$ acyl, cyano, nitro or —$NR_5R_6$, where $R_5$ and $R_6$ represent hydrogen or $C_1$-$C_3$ alkyl respectively;
  $R_4$ represents hydrogen or $C_1$-$C_4$ alkyl;
  $R_2$ represents hydrogen or —$CH_2N(R_7)_2$, where $R_7$ is $C_1$-$C_3$ alkyl.

Further, n is 0 or 1;
$R_1$ represents

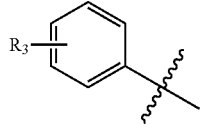

or thiophene, furan, pyrrole, pyridine, thiazole, imidazole or cyclohexane substituted with $R_4$;
  wherein $R_3$ represents hydrogen or substituted hydroxyl, carboxyl, aldehyde group, fluorine, chlorine, bromine, iodine, methyl, isopropyl, trifluoromethyl, methoxy, methoxycarbonyl, acetyl, cyano, nitro or —$NR_5R_6$, where $R_5$ and $R_6$ represent hydrogen or methyl respectively;
  $R_4$ represents hydrogen;
  $R_2$ represents hydrogen or —$CH_2N(CH_3)_2$, —$CH_2N(C_2H_5)_2$, or —$CH_2N(C_3H_7)_2$.

Further, n is 0 or 1;
$R_1$ represents fluorine, phenyl mono- or poly-substituted with methyl, unsubstituted or methyl-substituted thiophene, furan, pyrrole, pyridine, thiazole, imidazole or cyclohexane;
$R_2$ represents —$CH_2N(CH_3)_2$, —$CH_2N(C_2H_5)_2$, or —$CH_2N(C_3H_7)_2$.

Further, the selective butyrylcholinesterase inhibitor having a general formula (I) or a pharmaceutically acceptable salt thereof are any one of the following:

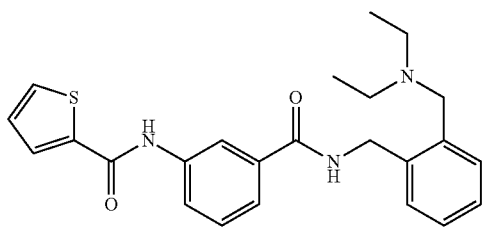

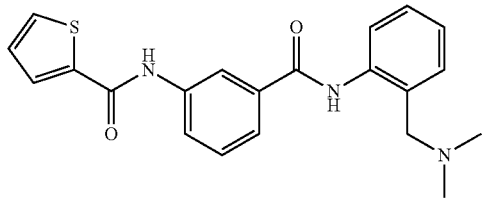

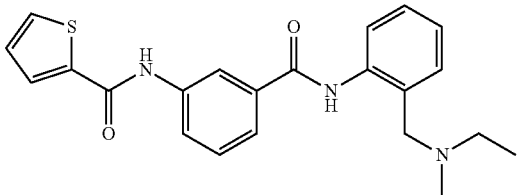

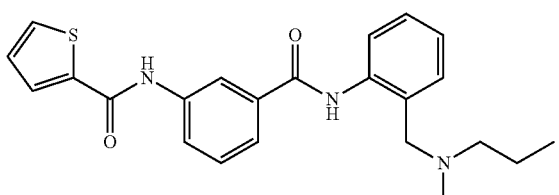

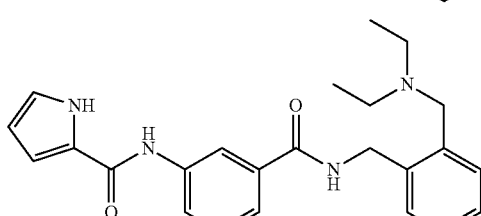

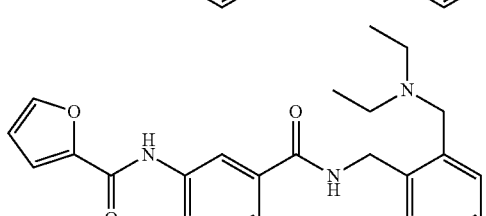

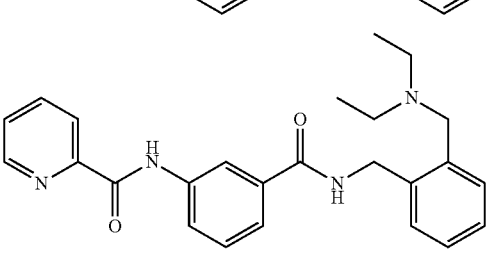

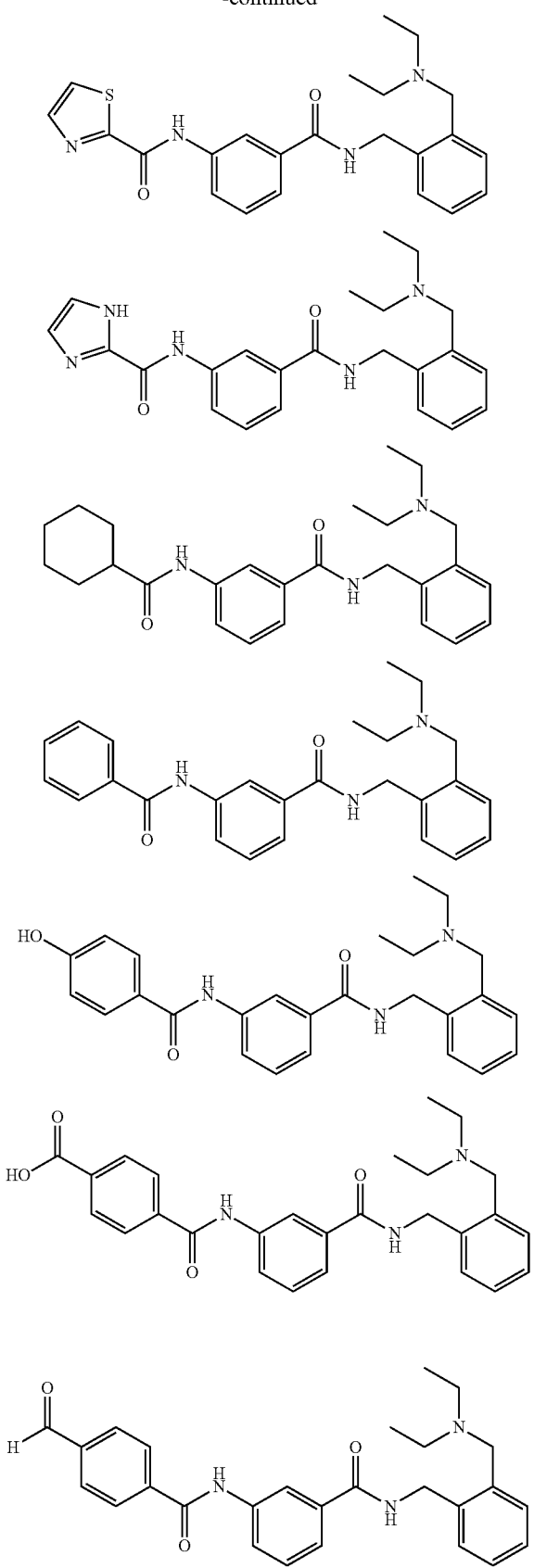
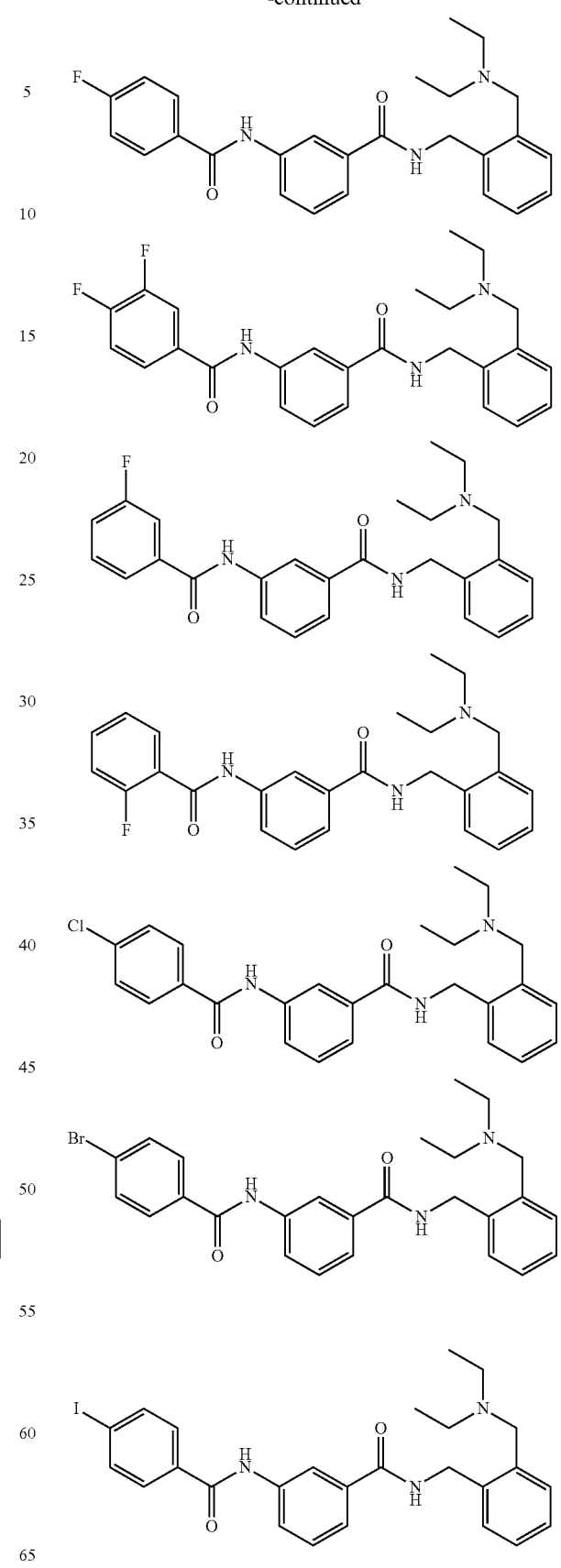

-continued
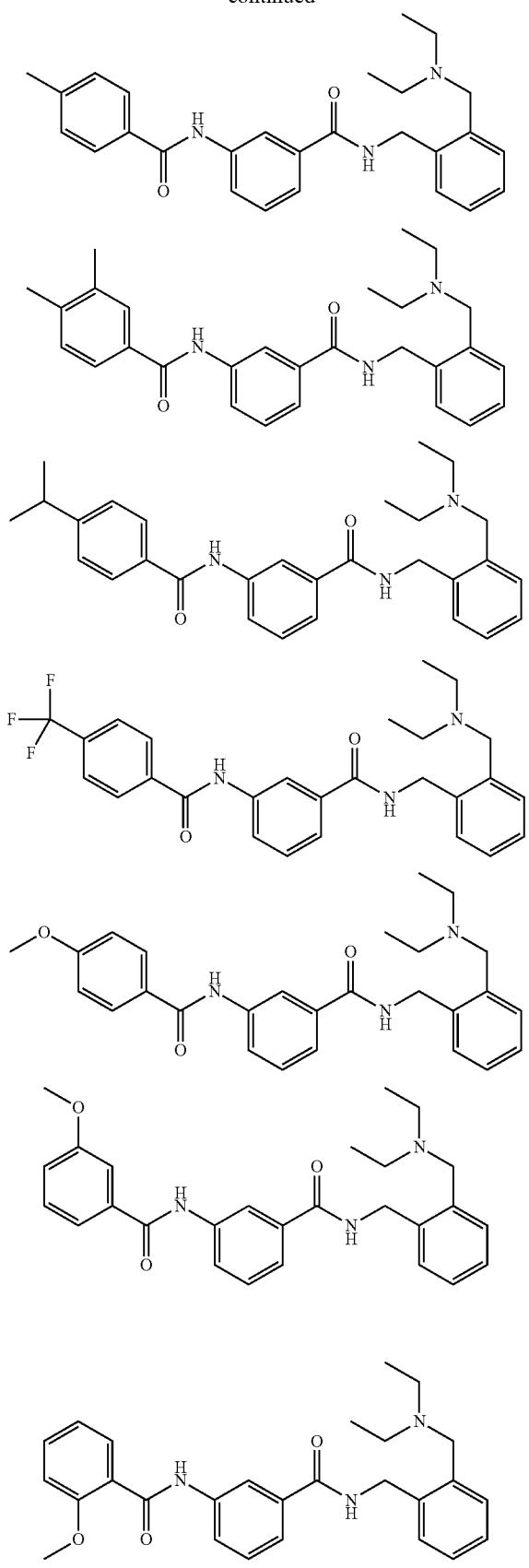
-continued
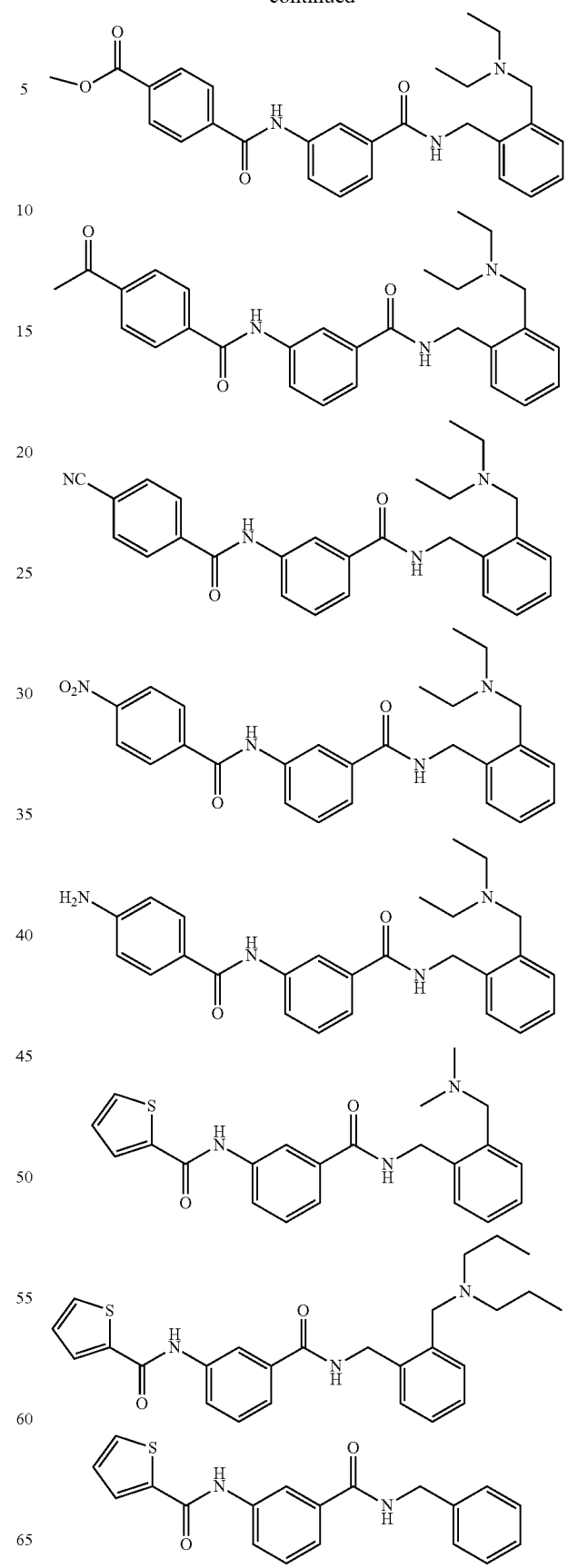

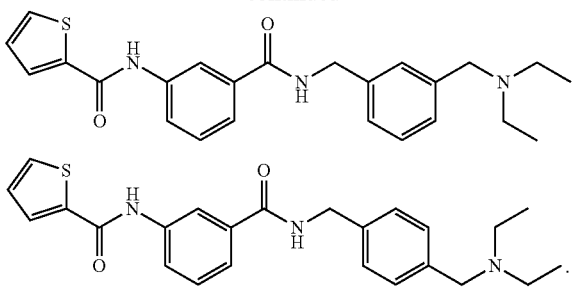

Further the Pharmaceutically acceptable salt of the selective butyrylcholinesterase inhibitor is hydrochloride, maleate or citrate.

A pharmaceutical composition containing a therapeutically effective amount of one or more selective butyrylcholinesterase inhibitors having a general formula (I) or a pharmaceutically acceptable salt thereof, and a pharmaceutically acceptable carrier.

A pharmaceutical composition containing a therapeutically effective amount of one or more selective butyrylcholinesterase inhibitors having a general formula (I) or a pharmaceutically acceptable salt thereof, and a pharmaceutically acceptable auxiliary material.

Further, the pharmaceutical composition is a tablet, capsule, powder, syrup, liquid, suspension or injection.

A method for preparing the selective butyrylcholinesterase inhibitor having a general formula (I) or a pharmaceutically acceptable salt thereof:

the reaction scheme is as follows:

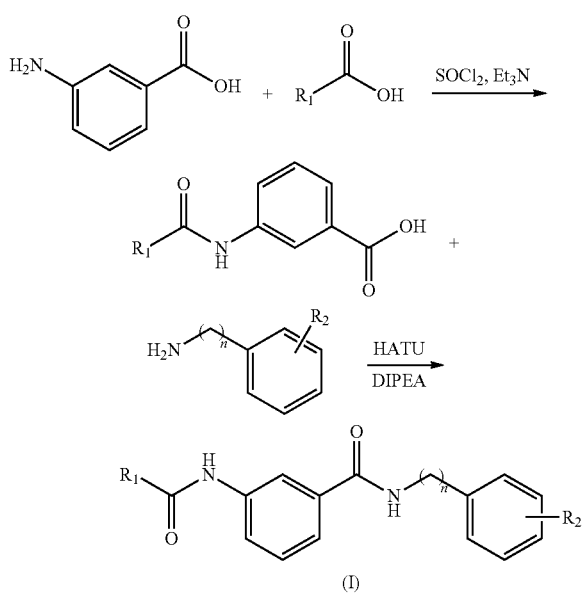

the preparation method comprises:

taking 3-aminobenzoic acid as a starting material, forming a corresponding amide intermediate with an aromatic acid having a different ring system and different substituents, and then reacting with an intermediate

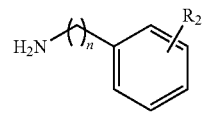

to prepare the selective butyrylcholinesterase inhibitor having a general formula (I) or a pharmaceutically acceptable salt thereof.

Use of the selective butyrylcholinesterase inhibitor having a general formula (I) or a pharmaceutically acceptable salt thereof in the preparation of a medicine for treating Alzheimer's disease.

Beneficial effects: The compound of the present invention or a pharmaceutically acceptable salt thereof has good target activity in vitro, extremely high selectivity and drug safety, and can be used as a lead substance for the further development of treatment of Alzheimer's disease through selectively inhibiting butyrylcholinesterase.

DETAILED DESCRIPTION OF THE INVENTION

Example 1

(1) Synthesis of 3-(thiophen-2-carboxamido)benzoic acid (Intermediate 1)

3-aminobenzoic acid (1 g, 7.29 mmol) was placed in an eggplant-shaped flask and dissolved with tetrahydrofuran (10 mL). Triethylamine (0.89 g, 8.75 mmol) was added and a solution of thiophene-2-formyl chloride (1.28 g, 8.75 mmol) in tetrahydrofuran was added dropwise under an ice bath. After completion of the dropwise addition, the mixture was stirred at normal temperature for 2 hours. After completion of the reaction, the tetrahydrofuran was removed under reduced pressure, dichloromethane was added, the mixture was filtered with suction, the filter cake was washed twice with dichloromethane, and dried to obtain 3-(thiophen-2-carboxamido)benzoic acid (1.7 g, yield 94.44%) as a white solid. $^1$H NMR (500 MHz, DMSO-d6): δ 13.04 (s, 1H, OH), 10.42 (s, 1H, NH), 8.35 (t, J=1.5 Hz, 1H, ArH), 8.07 (dd, $J_1$=1 Hz, $J_2$=4 Hz, 1H, ArH), 8.03 (dd, $J_1$=1 Hz, $J_2$=8 Hz, 1H, ArH), 7.89 (dd, $J_1$=1 Hz, $J_2$=4.5 Hz, 1H, ArH), 7.68 (d, J=8 Hz, 1H, ArH), 7.49 (t, J=4 Hz, 1H, ArH), 7.24 (t, J=4.5 Hz, 1H, ArH). MS (ESI): calcd. for $C_{12}H_9NO_3S[M+H]^+$ 248.0303 found 248.0720.

(2) Synthesis of N-(2-(aminomethyl)benzyl)-N-ethylethylamine (Intermediate 2)

2-cyanobenzyl bromide (750 mg, 3.47 mmol) was placed in an eggplant-shaped flask and dissolved with acetonitrile (10 mL). Potassium carbonate (500 mg, 3.62 mmol) was added, a solution of diethylamine (256 mg, 3.5 mmol) in acetonitrile (2 mL) was added dropwise under stirring. After completion of the dropwise addition, the mixture was stirred at normal temperature overnight. After completion of the reaction, suction filtration was performed with diatomaceous earth, and the solvent was removed under reduced pressure to obtain a crude product. The solution of the obtained crude product in anhydrous ether (5 mL) was added dropwise to a suspension of lithium aluminum hydride (0.3 g, 8 mmol) in anhydrous ether (10 mL) under an ice bath. After completion of the dropwise addition, the mixture was stirred at room temperature for 12 hours. After completion of the reaction, 20% sodium hydroxide solution (5 mL) was added dropwise to the reaction flask under an ice bath, and extracted with ether (10 mL each) for three times. The combined organic phase was dried with anhydrous sodium sulfate and separated by silica gel column chromatography to obtain the intermediate N-(2-(aminomethyl)benzyl)-N-ethylethylamine (460 mg, yield 62.50%). $^1$H NMR (500 MHz, CDCl3): δ 7.28 (dd, $J_1$=1.5 Hz, $J_2$=7.5 Hz, 2H, ArH), 7.25 (td, $J_1$=7.5 Hz, $J_2$=1.5 Hz, 2H, ArH), 3.84 (s, 2H, $CH_2$), 3.60 (s, 2H, $CH_2$), 2.52 (q, J=7 Hz, 4H, $CH_2$), 1.06 (t, J=7 Hz, 6H, $CH_3$). MS (ESI): calcd. for $C_{11}H_{20}N_2$ $[M+H]^+$ 193.1626 found 193.0690.

(3) Synthesis of N-(3-((2-((diethylamino)methyl) benzyl)carbamoyl)phenyl)thiophene-2-carboxamide 3-(thiophen-2-carboxamido)benzoic acid (250 mg, 1.01 mmol) was placed in an eggplant-shaped flask and dissolved with dichloromethane (5 mL). After that, 2-(7-oxobenzotriazole)-N,N,N',N'-tetramethylurea hexafluorophosphate (480 mg, 1.26 mmol) and N,N-diisopropylethylamine (163 mg, 1.26 mmol) were stirred at room temperature for 1 hour for activation. After completion of the activation, a solution of N-(2-(aminomethyl)benzyl)-N-ethylethylamine (194 mg, 1.01 mmol) in dichloromethane (2 mL) was added dropwise, and reacted at room temperature for 18 hours. The reaction solution was washed once with deionized water, once with a saturated sodium bicarbonate solution, and once with saturated brine, dried over anhydrous sodium sulfate, and separated by silica gel column chromatography to obtain N-(3-((2-((diethylamino)methyl)benzyl)carbamoyl)phenyl) thiophene-2-carboxamide (162 mg, yield 46.30%). $^1$H NMR (500 MHz, CDCl$_3$): δ 9.47 (s, 1H, NH), 8.53 (s, 1H, ArH), 8.16 (d, J=7.5 Hz, 1H, ArH), 7.95 (s, 1H, ArH), 7.77 (d, J=3.0 Hz, 1H, ArH), 7.56 (dd, $J_1$=5.0 Hz, $J_2$=1.0 Hz, 1H, ArH), 7.37 (dt, $J_1$=15.5 Hz, $J_2$=7.5 Hz, 4H, ArH), 7.25 (dd, $J_1$=10.0 Hz, $J_2$=4.0 Hz, 2H), 7.14 (dd, $J_1$=5.0 Hz, $J_2$=4.0 Hz, 1H), 4.61 (d, J=5.0 Hz, 2H, $CH_2$), 3.66 (s, 2H, $CH_2$), 2.60 (q, J=7.0 Hz, 4H, $CH_2$), 1.02 (t, J=7.0 Hz, 6H, $CH_3$). MS (ESI): calcd. for $C_{24}H_{27}N_3O_2S[M+H]^+$ 422.1824 found 422.2450.

Example 2

(1) Synthesis of N,N-dimethyl-1-(2-nitrophenyl)methylamine (Intermediate 3)

2-nitrobenzaldehyde (1.00 g, 6.62 mmol) was placed in an eggplant-shaped flask and dissolved with dichloroethane (95 mL). Dimethylamine (447 mg, 9.93 mmol) and zinc chloride (0.90 g, 6.62 mmol) were added. After stirring for 3 hours at room temperature, sodium cyanoborohydride (624 mg, 9.93 mmol) was added. After stirring at room temperature for 18 hours, a saturated sodium bicarbonate solution (40 mL) was added and the stirring was continued for one hour. The mixture was extracted with dichloromethane (100 mL), the organic phase was combined and washed twice with a saturated sodium bicarbonate solution, dried over anhydrous sodium sulfate, and separated by silica gel column chromatography to obtain N,N-dimethyl-1-(2-nitrophenyl)methylamine (940 mg, yield 79.10%). $^1$H NMR (500 MHz, CDCl$_3$): δ 7.85 (d, J=8.0 Hz, 1H, ArH), 7.63 (d, J=7.5 Hz, 1H, ArH), 7.57 (t, J=7.5 Hz, 1H, ArH), 7.41 (t, J=8.0 Hz, 1H, ArH), 3.73 (s, 2H, $CH_2$), 2.25 (s, 6H, $CH_3$). MS (ESI): calcd. for $C_{11}H_{16}N_2O_2$ $[M+H]^+$ 209.1212 found 209.2458.

(2) Synthesis of 2-((dimethylamino)methyl)aniline (Intermediate 4)

N,N-dimethyl-1-(2-nitrophenyl)methylamine (405 mg, 2.25 mmol) was placed in an eggplant-shaped flask and dissolved with absolute ethanol (45 mL). Ammonium formate (0.99 g, 15.75 mmol) and 10% palladium on carbon (177 mg, 0.17 mmol) were added. The mixture was stirred at room temperature for one hour, and suction filtration was performed with diatomaceous earth. The solvent was removed via rotary evaporation, and then the residue was dissolved in dichloromethane (30 mL), and washed with deionized water for three times. The organic phase was dried over anhydrous sodium sulfate and separated by silica gel column chromatography to obtain 2-((dimethylamino) methyl)aniline (212 mg, yield 63.10%). $^1$H NMR (500 MHz, CDCl$_3$): δ 6.93 (d, J=8.0 Hz, 1H, ArH), 6.74 (d, J=7.5 Hz, 1H, ArH), 6.68 (t, J=7.5 Hz, 1H, ArH), 6.53 (t, J=8.0 Hz, 1H, ArH), 3.66 (s, 2H, $CH_2$), 2.16 (s, 6H, $CH_3$). MS (ESI): calcd. for $C_{11}H_{18}N_2$ $[M+H]^+$ 179.1470 found 179.3024.

(2) Synthesis of N-(3-((2-((dimethylamino)methyl) phenyl)carbamoyl)phenyl)thiophene-2-carboxamide 3-(thiophen-2-carboxamido)benzoic acid (250 mg, 1.01 mmol) was placed in an eggplant-shaped flask and dissolved with dichloromethane (5 mL). After that, 2-(7-oxobenzotriazole)-N,N,N',N'-tetramethylurea hexafluorophosphate (480 mg, 1.26 mmol) and N,N-diisopropylethylamine (163 mg, 1.26 mmol) were added and stirred at room temperature for 1 hour for activation. After activation, a solution of N-(2-(aminomethyl)benzyl)-N-ethylethylamine (167 mg, 1.11 mmol) in dichloromethane (2 mL) was added dropwise, and reacted at room temperature for 18 hours. The reaction solution was washed once with deionized water, once with a saturated sodium bicarbonate solution and once with saturated brine, dried over anhydrous sodium sulfate, and separated by silica gel column chromatography to obtain N-(3-((2-((dimethylamino)methyl)phenyl)carbamoyl)phenyl)thiophene-2-carboxamide (207 mg, yield 54.11%). $^1$H NMR (500 MHz, CDCl$_3$): δ 11.92 (s, 1H, CONH), 8.44 (d, J=8.1 Hz, 1H, ArH), 8.30 (s, 1H, ArH), 8.15 (s, 1H, ArH), 8.08 (dd, $J_1$=8.1, $J_2$=1.4 Hz, 1H, ArH), 7.71 (dd, $J_1$=3.7, $J_2$=0.9 Hz, 1H, ArH), 7.63 (d, J=7.8 Hz, 1H, ArH), 7.55 (dd, $J_1$=5.0, $J_2$=0.9 Hz, 1H, ArH), 7.47 (t, J=7.8 Hz, 1H, ArH), 7.34 (m, 1H, ArH), 7.14 (d, J=6.7 Hz, 1H, ArH), 7.09 (dd, $J_1$=5.0, $J_2$=3.7 Hz, 1H, ArH), 7.05 (td, $J_1$=7.4, $J_2$=0.9 Hz, 1H, ArH), 3.60 (s, 2H, $CH_2$), 2.36 (s, 6H, $CH_3$). MS (ESI): calcd. for $C_{21}H_{21}N_3O_2S[M+H]^+$ 379.1354 found 379.3057.

Example 3

Synthesis of N-(3-((2-((diethylamino)methyl)phenyl)carbamoyl)phenyl)thiophene-2-carboxamide With reference to the synthesis method of Example 2, the intermediate 4 in Example 2 was replaced with 2-((diethylamino)methyl)aniline to obtain a yellow oily liquid compound, namely N-(3-((2-((diethylamino)methyl)phenyl)carbamoyl)phenyl)thiophene-2-carboxamide (Compound 3). There was one spot under TLC detection, there was a dark spot under ultraviolet light at 254 nm, and there was no fluorescence under 365 nm. $^1$H NMR (500 MHz, CDCl$_3$): δ 8.41 (d, J=8.0 Hz, 1H, ArH), 8.19 (d, J=8.0 Hz, 1H, ArH), 8.14 (s, 1H, ArH), 8.01 (d, J=1.5 Hz, 1H, ArH), 7.71 (m, 1H, ArH), 7.64 (d, J=8.0 Hz, 1H, ArH), 7.57 (d, J=5.0 Hz, 1H, ArH), 7.48 (t, J=7.8 Hz, 1H, ArH), 7.33 (t, J=7.8 Hz, 1H, ArH), 7.15 (m, 2H, ArH), 7.06 (t, J=7.4 Hz, 1H, ArH), 3.73 (s, 2H, CH$_2$), 2.65 (q, J=7.1 Hz, 4H, CH$_2$), 1.05 (t, J=7.1 Hz, 6H, CH$_3$). MS (ESI): calcd. for C$_{23}$H$_{25}$N$_3$O$_2$S[M+H]$^+$ 408.1667 found 408.2413.

Example 4

Synthesis of N-(3-((2-((dipropylamino)methyl)phenyl)carbamoyl)phenyl)thiophene-2-carboxamide With reference to the synthesis method of Example 2, the intermediate 4 in Example 2 was replaced with 2-((dipropylamino)methyl)aniline to obtain a yellow oily liquid compound, namely N-(3-((2-((dipropylamino)methyl)phenyl)carbamoyl)phenyl)thiophene-2-carboxamide (Compound 4). There was one spot under TLC detection, there was a dark spot under ultraviolet light at 254 nm, and there was no fluorescence under 365 nm. $^1$H NMR (500 MHz, CDCl$_3$): δ 11.71 (s, 1H, CONH), 8.41 (d, J=8.0 Hz, 1H, ArH), 8.18 (d, J=8.0 Hz, 1H, ArH), 8.02 (s, 1H, ArH), 7.99 (s, 1H, ArH), 7.69 (d, J=3.0 Hz, 1H, ArH), 7.63 (d, J=7.5 Hz, 1H, ArH), 7.58 (dd, J=5.0, 1.0 Hz, 1H, ArH), 7.48 (m, 1H, ArH), 7.34 (m, 2H, ArH), 7.14 (t, J=4.3 Hz, 1H, ArH), 7.06 (t, J=7.5 Hz, 1H, ArH), 3.74 (s, 2H, CH$_2$), 2.49 (m, 4H, CH$_2$), 1.50 (m, 4H, CH$_2$), 0.81 (t, J=7.3 Hz, 6H, CH$_3$). MS (ESI): calcd. for C$_{25}$H$_{29}$N$_3$O$_2$S[M+H]$^+$ 436.1980 found 436.4032.

Example 5

Synthesis of N-(3-((2-((diethylamino)methyl)benzyl)carbamoyl)phenyl-pyrrole-2-carboxamide With reference to the synthesis method of Example 1, the intermediate 1 in Example 1 was replaced with 3-(pyrazole-2-carboxamido)benzoic acid to obtain a pale yellow solid compound, namely N-(3-((2-((diethylamino)methyl)benzyl)carbamoyl)phenyl)-pyrrole-2-carboxamide (Compound 5). There was one spot under TLC detection, there was a dark spot under ultraviolet light at 254 nm, and there was no fluorescence under 365 nm. $^1$H NMR (300 MHz, DMSO-d6): δ 11.30 (s, 1H, ArH), 9.86 (s, 1H, NHCO), 8.74 (s, 1H, NHCO), 8.13 (t, J=1.5 Hz, 1H, ArH)7.91 (q, J$_1$=1.5 Hz, J$_2$=1.5 Hz, J$_3$=7.5 Hz, 1H, ArH), 7.79 (q, J$_1$=1.5 Hz, J$_2$=1.5 Hz, J$_3$=7.5 Hz, 1H, ArH), 7.56 (dd, J$_1$=1.5 Hz, J$_2$=7.5 Hz, 1H, ArH), 7.45 (t, J=7.5 Hz, 1H, ArH), 7.44(dd, J$_1$=1.5 Hz, J$_2$=7.5 Hz, 1H, ArH), 7.43 (dd, J$_1$=1.5 Hz, J$_2$=7.5 Hz, 2H, ArH), 7.37(q, J$_1$=1.5 Hz, J$_2$=1.5 Hz, J$_3$=7.5 Hz, 2H, ArH), 6.42 (t, J=7.5 Hz, 1H, ArH), 4.47 (s, 2H, CH$_2$), 3.66 (s, 2H, CH$_2$), 2.56 (d, J=8.0 Hz, 4H, CH$_2$), 1.02 (d, J=8.0 Hz, 6H, CH$_3$). HR-MS (ESI): calcd. for C$_{24}$H$_{28}$N$_4$O$_2$ [M+H$^+$] 405.2212 found 405.0745.

Example 6

Synthesis of N-(3-((2-((diethylamino)methyl)benzyl)carbamoyl)phenyl)furan-2-carboxamide With reference to the synthesis method of Example 1, the intermediate 1 in Example 1 was replaced with 3-(furan-2-carboxamido)benzoic acid to obtain a yellow oily liquid compound, namely N-(3-((2-((diethylamino)methyl)benzyl)carbamoyl)phenyl)furan-2-carboxamide (Compound 6). There was one spot under TLC detection, there was a dark spot under ultraviolet light at 254 nm, and there was no fluorescence under 365 nm. $^1$H NMR (500 MHz, CDCl$_3$): δ 9.40 (s, 1H, CONH), 8.22 (s, 1H, ArH), 8.07 (dd, J$_1$=8.0, J$_2$=1.0 Hz, 1H, ArH), 7.88 (s, 1H, ArH), 7.54 (d, J=1.0 Hz, 1H, ArH), 7.49 (d, J=7.4 Hz, 1H, ArH), 7.45 (d, J=7.8 Hz, 1H, ArH), 7.38 (t, J=7.8 Hz, 1H, ArH), 7.32 (m, 1H, ArH), 7.27 (dd, J$_1$=7.4, J$_2$=1.9 Hz, 2H, ArH), 6.58 (dd, J$_1$=3.5, J$_2$=1.9 Hz, 1H, ArH), 4.68 (d, J=4.8 Hz, 2H, CH$_2$), 3.67 (s, 2H, CH$_2$), 2.61 (dd, J=14.0, 7.0 Hz, 4H, CH$_2$), 1.03 (t, J=7.0 Hz, 6H, CH$_3$). MS (ESI): calcd. for C$_{24}$H$_{27}$N$_3$O$_3$ [M+H]$^+$ 406.2052 found 406.2413.

Example 7

Synthesis of N-(3-((2-((diethylamino)methyl)benzyl)carbamoyl)phenyl-pyridineamide With reference to the synthesis method of Example 1, the intermediate 1 in Example 1 was replaced with 3-(pyridine-2-carboxamido)benzoic acid to obtain a pale yellow solid compound, namely N-(3-((2-((diethylamino)methyl)benzyl)carbamoyl)phenyl)-pyridineamide (Compound 7). There was one spot under TLC detection, there was a dark spot under ultraviolet light at 254 nm, and there was no fluorescence under 365 nm. $^1$H NMR (300 MHz, DMSO-d6): δ 9.86 (s, 1H, NHCO), 8.77 (dd, J$_1$=1.5 Hz, J$_2$=7.5 Hz, 1H, ArH), 8.74 (s, 1H, NHCO), 8.37 (dd, J$_1$=1.5 Hz, J$_2$=7.5 Hz, 1H, ArH), 8.13 (t, J=1.5H, 1H, ArH), 8.13 (t, J=1.5H, 1H, ArH), 8.02 (q, J$_1$=1.5 Hz, J$_2$=7.5 Hz, J$_3$=7.5 Hz, 1H, ArH), 7.93 (q, J$_1$=1.5 Hz, J$_2$=7.5 Hz, J$_3$=7.5 Hz, 1H, ArH), 7.91 (q, J$_1$=1.5 Hz, J$_2$=1.5 Hz, J$_3$=7.5 Hz, 1H, NHCO) 7.79 (q, J$_1$=1.5 Hz, J$_2$=7.5 Hz, J$_3$=1.5 Hz, 1H, ArH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=7.5 Hz, J$_3$=7.5 Hz, 2H, ArH), 4.47 (s, 2H, CH$_2$), 3.66 (s, 2H, CH$_2$), 2.54 (d, J=8.0 Hz, 4H, CH$_2$), 1.02 (d, J=8.0 Hz, 6H, CH$_3$).HR-MS (ESI): calcd. for C$_{24}$H$_{28}$N$_4$O$_2$ [M+H$^+$] 417.2212 found 417.3052.

Example 8

Synthesis of N-(3-((2-((diethylamino)methyl)benzyl)carbamoyl)phenyl-thiazole-2-carboxamide With reference to the synthesis method of Example 1, the intermediate 1 in Example 1 was replaced with 3-(thiazol-2-carboxamido)benzoic acid to obtain a pale yellow solid compound, namely N-(3-((2-((diethylamino)methyl)benzyl)carbamoyl)phenyl)-thiazole-2-carboxamide (Compound 8). There was one spot under TLC detection, there was a dark spot under ultraviolet light at 254 nm, and there was no fluorescence under 365 nm. $^1$H NMR (300 MHz, DMSO-d6): δ10.81 (s, 1H, NHCO), 8.74 (s, 1H, NHCO), 8.19 (d, J=7.5 Hz, 1H, ArH), 8.13 (t, J=1.5H, 1H, ArH), 7.91 (q, J$_1$=1.5 Hz, J$_2$=1.5 Hz, J$_3$=7.5 Hz, 1H, ArH), 7.81 (d, J=7.5 Hz, 1H, ArH), 7.79 (q, J$_1$=1.5 Hz, J$_2$=1.5 Hz, J$_3$=7.5 Hz, 1H, ArH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=1.5 Hz, J$_3$=7.5 Hz, 2H, ArH), 4.47 (s, 2H, CH$_2$), 3.66 (s, 2H, CH$_2$), 2.54 (d, J=8.0

Hz, 4H, CH$_2$), 1.02 (d, J=8.0 Hz, 6H, CH$_3$).HR-MS (ESI): calcd. for C$_{24}$H$_{28}$N$_4$O$_2$[M+H$^+$] 423.1776 found 423.5935.

Example 9

Synthesis of N-(3-((2-((diethylamino)methyl)benzyl)carbamoyl)phenyl)-imidazole-2-carboxamide With reference to the synthesis method of Example 1, the intermediate 1 in Example 1 was replaced with 3-(imidazole-2-carboxamido)benzoic acid to obtain a pale yellow solid compound, namely N-(3-((2-((diethylamino)methyl)benzyl)carbamoyl)phenyl)-imidazole-2-carboxamide (Compound 9). There was one spot under TLC detection, there was a dark spot under ultraviolet light at 254 nm, and there was no fluorescence under 365 nm. $^1$H NMR (300 MHz, DMSO-d6): δ 10.81 (s, 1H, NHCO), 8.74 (s, 1H, NHCO), 8.13 (t, J=1.5H, 1H, ArH), 7.91 (q, J$_1$=1.5 Hz, J$_2$=1.5 Hz, J$_3$=7.5 Hz, 1H, ArH), 7.79 (q, J$_1$=1.5 Hz, J$_2$=1.5 Hz, J$_3$=7.5 Hz, 1H, ArH), 7.63 (s, 1H, CHNHCH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=1.5 Hz, J$_3$=7.5 Hz, 2H, ArH), 7.18 (d, J=7.5 Hz, 1H, ArH), 6.84 (d, J=7.5 Hz, 1H, ArH), 4.47 (s, 2H, CH$_2$), 3.66 (s, 2H, CH$_2$), 2.54 (d, J=8.0 Hz, 4H, CH$_2$), 1.02 (d, J=8.0 Hz, 6H, CH$_3$).HR-MS (ESI): calcd. for C$_{24}$H$_{28}$N$_4$O$_2$[M+H$^+$] 406.2165 found 406.0414.

Example 10

Synthesis of 3-(cyclohexanecarboxamido)-N-(2-((diethylamino)methyl)benzyl)benzamide With reference to the synthesis method of Example 1, the intermediate 1 in Example 1 was replaced with 3-(cyclohexane-2-carboxamido)benzoic acid to obtain a pale yellow solid compound, namely 3-(cyclohexanecarboxamido)-N-(2-((diethylamino)methyl)benzyl)benzamide (Compound 10). There was one spot under TLC detection, there was a dark spot under ultraviolet light at 254 nm, and there was no fluorescence under 365 nm. $^1$H NMR (300 MHz, DMSO-d6): δ 10.05 (s, 1H, NHCO), 8.74 (s, 1H, NHCO), 8.13 (t, J=1.5H, 1H, ArH), 7.79 (q, J$_1$=1.5 Hz, J$_2$=1.5 Hz, J$_3$=7.5 Hz, 1H, ArH), 7.78 (q, J$_1$=1.5 Hz, J$_2$=1.5 Hz, J$_3$=7.5 Hz, 1H, ArH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=1.5 Hz, J$_3$=7.5 Hz, 2H, ArH),4.47 (s, 2H, CH$_2$), 3.66 (s, 2H, CH$_2$), 2.54 (d, J=7.0 Hz, 4H, CH$_2$), 1.70 (dd, J$_1$=7.0 Hz, J$_2$=7.1 Hz, 4H, CH$_2$), 1.48 (t, J=7.1H, 4H, CH$_2$), 1.45 (t, J=7.1H, 4H, CH$_2$), 1.02 (d, J=8.0 Hz, 6H, CH$_3$).HR-MS (ESI): calcd. for C$_{24}$H$_{28}$N$_4$O$_2$[M+H$^+$] 422.2729 found 422.0368.

Example 11

Synthesis of 3-benzamido-N-(2-((diethylamino)methyl)benzyl)benzamide

With reference to the synthesis method of Example 1, the intermediate 1 in Example 1 was replaced with 3-(phenyl-2-carboxamido)benzoic acid to obtain a pale yellow solid compound, namely 3-benzamido-N-(2-((diethylamino)methyl)benzyl)benzamide (Compound 11). There was one spot under TLC detection, there was a dark spot under ultraviolet light at 254 nm, and there was no fluorescence under 365 nm. $^1$H NMR (300 MHz, DMSO-d6): δ 10.4 (s, 1H, NHCO), 8.74 (s, 1H, NHCO), 8.13 (t, J=1.5H, 1H, ArH), 7.96 (q, J$_1$=1.5 Hz, J$_2$=1.5 Hz, J$_3$=7.5 Hz, 2H, ArH), 7.91 (q, J$_1$=1.5 Hz, J$_2$=1.5 Hz, J$_3$=7.5 Hz, 1H, ArH), 7.79 (q, J$_1$=1.5 Hz, J$_2$=1.5 Hz, J$_3$=7.5 Hz, 1H, ArH), 7.62 (m, J$_1$=1.5 Hz, J$_2$=1.5 Hz, J$_3$=7.5 Hz, J$_4$=7.5 Hz 2H, ArH), 7.54 (q, J$_1$=1.5 Hz, J$_2$=1.5 Hz, J$_3$=7.5 Hz, 2H, ArH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=1.5 Hz, J$_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$).HR-MS (ESI): calcd. for C$_{24}$H$_{28}$N$_4$O$_2$[M+H$^+$] 416.2260 found 416.9463.

Example 12

Synthesis of N-(2-((diethylamino)methyl)benzyl)-3-(4-hydroxybenzamido)benzamide

With reference to the synthesis method of Example 1, the intermediate 1 in Example 1 was replaced with 3-(hydroxyphenyl-2-carboxamido)benzoic acid to obtain a pale yellow solid compound, namely N-(2-((diethylamino)methyl)benzyl)-3-(4-hydroxybenzamido)benzamide (Compound 12). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 9.68 (s, 1H, OH), 8.13 (t, J=1.5H, 1H, ArH), 7.91 (q, J$_1$=1.5 Hz, J$_2$=1.5 Hz, J$_3$=7.5 Hz, 1H, ArH), 7.79 (q, J$_1$=1.5 Hz, J$_2$=1.5 Hz, J$_3$=7.5 Hz, 1H, ArH), 7.76 (dd, J$_1$=1.5 Hz, J$_2$=7.5 Hz, 2H, ArH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=1.5 Hz, J$_3$=7.5 Hz, 2H, ArH), 6.88 (dd, J$_1$=1.5 Hz, J$_2$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$).HR-MS (ESI): calcd. for C$_{24}$H$_{28}$N$_4$O$_2$ [M+H$^+$] 432.2209 found 432.9846.

Example 13

Synthesis of 4-((3-((2-((diethylamino)methyl)benzyl)carbamoyl)phenyl)carbamoyl)benzoic acid With reference to the synthesis method of Example 1, the Intermediate 1 in Example 1 was replaced with 3-(-carboxybenzamido)benzoic acid to obtain a pale yellow solid compound, namely 4-((3-((2-((diethylamino)methyl)benzyl)carbamoyl)phenyl)carbamoyl)benzoic acid (Compound 13). There was one spot under TLC detection, there was a dark spot under ultraviolet light at 254 nm, and there was no fluorescence under 365 nm. $^1$H NMR (300 MHz, DMSO-d6): δ 12.71 (s, 1H, COOH), 10.40 (s, 1H, NHCO), 8.74 (s, 1H, NHCO), 8.21 (dd, J$_1$=1.5 Hz, J$_2$=7.5 Hz, 1H, ArH), 8.13 (t, J=1.5H, 1H, ArH), 8.06 (dd, J$_1$=1.5 Hz, J$_2$=7.5 Hz, 2H, ArH), 7.91 (q, J$_1$=1.5 Hz, J$_2$=1.5 Hz, J$_3$=7.5 Hz, 1H, ArH), 7.79 (q, J$_1$=1.5 Hz, J$_2$=1.5 Hz, J$_3$=7.5 Hz, 1H, ArH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=1.5 Hz, J$_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$).HR-MS (ESI): calcd. for C$_{24}$H$_{28}$N$_4$O$_2$ [M+H$^+$] 460.2158 found 460.4872.

Example 14

Synthesis of N-(2-((diethylamino)methyl)benzyl)-3-(4-formanilide)benzamide

With reference to the synthesis method of Example 1, the intermediate 1 in Example 1 was replaced with 3-(4-formylbenzamido)benzoic acid to obtain a pale yellow solid compound, namely N-(2-((diethylamino)methyl)benzyl)-3-(4-formanilide)benzamide (Compound 14). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 9.89 (s, 1H, CHO), 8.74 (s, 1H, NHCO), 8.19 (dd, $J_1$=1.5 Hz, $J_2$=7.5 Hz, 2H, ArH), 8.13 (t, J=1.5Hz, 1H, ArH), 8.03 (dd, $J_1$=1.5 Hz, $J_2$=7.5 Hz, 2H, ArH), 7.91 (q, $J_1$=1.5 Hz, $J_2$=1.5 Hz, $J_3$=7.5 Hz, 1H, ArH), 7.79 (q, $J_1$=1.5 Hz, $J_2$=1.5 Hz, $J_3$=7.5 Hz, 1H, ArH), 7.45 (t, J=1.5Hz, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$).HR-MS (ESI): calcd. for C$_{24}$H$_{28}$N$_4$O$_2$[M+H$^+$] 444.2209 found 444.3533.

Example 15

Synthesis of N-(2-((diethylamino)methyl)benzyl)-3-(4-fluorobenzamido)benzamide

With reference to the synthesis method of Example 1, the intermediate 1 in Example 1 was replaced with 3-(4-fluorobenzamido)benzoic acid to obtain a yellow oily liquid compound, namely N-(2-((diethylamino)methyl)benzyl)-3-(4-fluorobenzamido)benzamide (Compound 15). There was one spot under TLC detection, there was a dark spot under ultraviolet light at 254 nm, and there was no fluorescence under 365 nm. $^1$H NMR (500 MHz, CDCl$_3$): δ 9.47 (s, 1H, CONH), 8.49 (s, 1H, ArH), 8.16 (d, J=7.2 Hz, 1H, ArH), 7.95 (t, J=7.2 Hz, 3H, ArH), 7.40 (dt, $J_1$=17.6, $J_2$=7.8 Hz, 3H, ArH), 7.25 (m, 2H, ArH), 7.17 (t, J=8.5 Hz, 2H, ArH), 4.58 (d, J=4.7 Hz, 2H, CH$_2$), 3.70 (s, 2H, CH$_2$), 2.64 (q, J=6.8 Hz, 4H, CH$_2$), 1.05 (t, J=6.8 Hz, 6H, CH$_3$). MS (ESI): calcd. for C$_{26}$H$_{28}$FN$_3$O$_2$[M+H]$^+$ 434.2166 found 434.5021.

Example 16

Synthesis of N-(3-((2-(diethylamino)methyl)benzyl)carbamoyl)phenyl)-3,4-difluorobenzamide With reference to the synthesis method of Example 1, the intermediate 1 in Example 1 was replaced with 3-(3,4-difluorobenzamido)benzoic acid to obtain a pale yellow solid compound, namely N-(3-((2-(diethylamino)methyl)benzyl)carbamoyl)phenyl)-3,4-difluorobenzamide (Compound 16). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 7.91 (q, $J_1$=1.5 Hz, $J_2$=1.5 Hz, $J_3$=7.5 Hz, 1H, ArH), 7.89 (q, $J_1$=1.5 Hz, $J_2$=5.0 Hz, $J_3$=7.5 Hz, 1H, ArH), 7.79 (q, $J_1$=1.5 Hz, $J_2$=1.5 Hz, $J_3$=7.5 Hz, 1H, ArH), 7.59 (q, $J_1$=1.5 Hz, $J_2$=5.0 Hz, $J_3$=8.0 Hz, 1H, ArH), 7.45 (t, J=1.5Hz, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 7.36 (q, $J_1$=5.0 Hz, $J_2$=7.5 Hz, $J_3$=8.0 Hz, 1H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$).HR-MS (ESI): calcd. for C$_{24}$H$_{28}$N$_4$O$_2$ [M+H$^+$] 452.2071 found 452.9844.

Example 17

Synthesis of N-(2-((diethylamino)methyl)benzyl)-3-(3-fluorobenzamido)benzamide

Referring to the synthesis method of Example 1, the intermediate 1 in Example 1 was replaced with 3-(3-fluorobenzamido)benzoic acid to obtain a yellow oily liquid compound, namely N-(2-((diethylamino)methyl)benzyl)-3-(3-fluorobenzamido)benzamide (Compound 17). There was one spot under TLC detection, there was a dark spot under ultraviolet light at 254 nm, and there was no fluorescence under 365 nm. $^1$H NMR (500 MHz, CDCl$_3$): δ 9.54 (s, 1H, CONH), 8.47 (s, 1H, ArH), 8.19 (d, J=7.0 Hz, 1H, ArH), 7.95 (t, J=7.0 Hz, 3H, ArH), 7.38 (dt, $J_1$=17.5, $J_2$=8.0 Hz, 3H, ArH), 7.25 (m, 2H, ArH), 7.20 (t, J=8.5 Hz, 2H, ArH), 4.44 (d, J=4.7 Hz, 2H, CH$_2$), 3.65 (s, 2H, CH$_2$), 2.62 (q, J=6.8 Hz, 4H, CH$_2$), 1.05 (t, J=6.8 Hz, 6H, CH$_3$). MS (ESI): calcd. for C$_{26}$H$_{28}$FN$_3$O$_2$[M+H]$^+$ 434.2166 found 434.5022.

Example 18

Synthesis of N-(3-((2-((diethylamino)methyl)benzyl)carbamoyl)phenyl)-2-fluorobenzamide With reference to the synthesis method of Example 1, the intermediate 1 in Example 1 was replaced with 3-(2-fluorobenzamido)benzoic acid to obtain a pale yellow solid compound, namely N-(3-((2-((diethylamino)methyl)benzyl)carbamoyl)phenyl)-2-fluorobenzamide (Compound 18). There was one spot under TLC detection, there was a dark spot under ultraviolet light at 254 nm, and there was no fluorescence under 365 nm. $^1$H NMR (300 MHz, DMSO-d6): δ 10.32 (s, 1H, NHCO), 8.74 (s, 1H, NHCO), 8.14 (q, $J_1$=1.5 Hz, $J_2$=5.0 Hz, $J_3$=7.5 Hz, 1H, ArH), 8.13 (t, J=1.5Hz, 1H, ArH), 7.91 (q, $J_1$=1.5 Hz, $J_2$=1.5 Hz, $J_3$=7.5 Hz, 1H, ArH), 7.79 (q, $J_1$=1.5 Hz, $J_2$=1.5 Hz, $J_3$=7.5 Hz, 1H, ArH), 7.51 (m, $J_1$=1.5 Hz, $J_2$=5.0 Hz, $J_3$=7.5 Hz, $J_4$=7.5 Hz, 1H, ArH), 7.45 (t, J=1.5Hz, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 7.29 (q, $J_1$=1.5 Hz, $J_2$=7.5 Hz, $J_3$=7.5 Hz, 1H, ArH), 7.15 (q, $J_1$=1.5 Hz, $J_2$=1.5 Hz, $J_3$=7.5 Hz, 1H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$).HR-MS (ESI): calcd. for C$_{24}$H$_{28}$N$_4$O$_2$ [M+H$^+$] 434.2166 found 434.8462.

Example 19

Synthesis of 3-(4-chlorobenzamido)-N-(2-((diethylamino)methyl)benzyl)benzamide

Referring to the synthesis method of Example 1, the intermediate 1 in Example 1 was replaced with 3-(2-chlorobenzamido)benzoic acid to obtain a pale yellow solid compound, namely 3-(4-chlorobenzamido)-N-(2-((diethylamino)methyl)benzyl)benzamide (Compound 19). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5Hz, 1H, ArH), 7.91 (q, $J_1$=1.5 Hz, $J_2$=1.5 Hz, $J_3$=7.5 Hz, 1H, ArH), 7.90 (dd, $J_1$=1.5 Hz, $J_2$=7.5 Hz, 2H, ArH), 7.79 (q, $J_1$=1.5 Hz, $J_2$=1.5 Hz, $J_3$=7.5 Hz, 1H, ArH), 7.55 (dd, $J_1$=1.5 Hz, $J_2$=7.5 Hz, 2H, ArH), 7.45 (t, J=1.5Hz, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$).HR-MS (ESI): calcd. for C$_{24}$H$_{28}$N$_4$O$_2$ [M+H$^+$] 450.1870 found 450.3457.

Example 20

Synthesis of 3-(4-bromobenzamido)-N-(2-((diethylamino)methyl)benzyl)benzamide

Referring to the synthesis method of Example 1, the intermediate 1 in Example 1 was replaced with 3-(2-bromobenzamido)benzoic acid to obtain a pale yellow solid compound, namely 3-(4-bromobenzamido)-N-(2-((diethylamino)methyl)benzyl)benzamide (Compound 20). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 7.91 (q, $J_1$=1.5 Hz, $J_2$=1.5 Hz, $J_3$=7.5 Hz, 1H, ArH), 7.84 (dd, $J_1$=1.5 Hz, $J_2$=7.5 Hz, 2H, ArH), 7.79 (q, $J_1$=1.5 Hz, $J_2$=1.5 Hz, $J_3$=7.5 Hz, 1H, ArH), 7.70 (dd, $J_1$=1.5 Hz, $J_2$=7.5 Hz, 2H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for C$_{24}$H$_{28}$N$_4$O2[M+H$^+$] 494.1365 found 494.6042.

Example 21

Synthesis of 3-(4-iodobenzamido)-N-(2-((diethylamino)methyl)benzyl)benzamide

With reference to the synthesis method of Example 1, the intermediate 1 in Example 1 was replaced with 3-(2-iodobenzamido)benzoic acid to obtain a pale yellow solid compound, namely 3-(4-iodobenzamido)-N-(2-((diethylamino)methyl)benzyl)benzamide (Compound 21). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 7.91 (q, $J_1$=1.5 Hz, $J_2$=1.5 Hz, $J_3$=7.5 Hz, 1H, ArH), 7.95 (q, $J_1$=1.5 Hz, $J_2$=7.5 Hz, 2H, ArH), 7.79 (q, $J_1$=1.5 Hz, $J_2$=1.5 Hz, $J_3$=7.5 Hz, 1H, ArH), 7.76 (dd, $J_1$=1.5 Hz, $J_2$=7.5 Hz, 2H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for C$_{24}$H$_{28}$N$_4$O$_2$ [M+H$^+$] 542.1226 found 542.5073.

Example 22

Synthesis of N-(2-((diethylamino)methyl)benzyl)-3-(4-methylbenzamido)benzamide

With reference to the synthesis method of Example 1, the intermediate 1 in Example 1 was replaced with 3-(4-methylbenzamido)benzoic acid to obtain a yellow oily liquid compound, namely N-(2-((diethylamino)methyl)benzyl)-3-(4-methylbenzamido)benzamide (Compound 22). There was one spot under TLC detection, there was a dark spot under ultraviolet light at 254 nm, and there was no fluorescence under 365 nm. $^1$H NMR (500 MHz, DMSO): δ 10.48 (s, 1H, CONH), 9.62 (s, 1H, CONH), 8.31 (s, 1H, ArH), 7.85 (d, J=7.5 Hz, 1H, ArH), 7.60 (d, J=7.5 Hz, 1H, ArH), 7.56 (d, J=8.0 Hz, 1H, ArH), 7.50 (m, 2H, ArH), 7.46 (d, J=9.0 Hz, 2H, ArH), 7.40 (m, 2H, ArH), 7.32 (d, J=8.0 Hz, 2H, ArH), 4.53 (d, J=5.7 Hz, 2H, CH$_2$), 3.66 (s, 2H, CH$_2$), 2.51 (q, J=7.0 Hz, 4H, CH$_2$), 2.39 (s, 3H, CH$_3$), 1.31 (t, J=7.0 Hz, 6H, CH$_3$). MS (ESI): calcd. for C$_{27}$H$_{31}$N$_3$O$_2$ [M+H]$^+$ 430.2416 found 430.3461.

Example 23

Synthesis of N-(3-((2-((diethylamino)methyl)benzyl)carbamoyl)phenyl)-3,4-dimethylbenzamide With reference to the synthesis method of Example 1, the intermediate 1 in Example 1 was replaced with 3-(3,4-dimethylbenzamido)benzoic acid to obtain a pale yellow solid compound, namely N-(3-((2-((diethylamino)methyl)benzyl)carbamoyl)phenyl)-3,4-dimethylbenzamide (Compound 23). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 7.91 (q, $J_1$=1.5 Hz, $J_2$=1.5 Hz, $J_3$=7.5 Hz, 1H, ArH), 7.79 (q, $J_1$=1.5 Hz, $J_2$=1.5 Hz, $J_3$=7.5 Hz, 1H, ArH), 7.76 (dd, $J_1$=1.5 Hz, $J_2$=7.5 Hz, 2H, ArH), 7.74 (dd, $J_1$=1.5 Hz, $J_2$=7.5 Hz, 1H, ArH), 7.45 (t, J=1.5H, 1H, ArH), 7.43 (dd, $J_1$=1.5 Hz, $J_2$=7.5 Hz, 2H, ArH), 7.39 (d, J=7.5 Hz, 1H, ArH), 7.37 (q, $J_1$=1.5 Hz, $J_2$=1.5 Hz, $J_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for C$_{24}$H$_{28}$N$_4$O$_2$ [M+H$^+$] 444.2573 found 444.4592.

Example 24

Synthesis of N-(2-((2-((diethylamino)methyl)benzyl)-3-(4-isopropylbenzamide)benzamide With reference to the synthesis method of Example 1, the intermediate 1 in Example 1 was replaced with 3-(4-isopropylbenzamido)benzoic acid to obtain a pale yellow solid compound, namely N-(2-((2-((diethylamino)methyl)benzyl)-3-(4-isopropylbenzamide)benzamide (Compound 24). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 7.91 (q, $J_1$=1.5 Hz, $J_2$=1.5 Hz, $J_3$=7.5 Hz, 1H, ArH), 7.89 (dd, $J_1$=1.5 Hz, $J_2$=7.5 Hz, 2H, ArH), 7.79 (q, $J_1$=1.5 Hz, $J_2$=1.5 Hz, $J_3$=7.5 Hz, 1H, ArH), 7.50 (dd, $J_1$=1.5 Hz, $J_2$=7.5 Hz, 2H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 5.0 (t, J=6.98 Hz, 1H, CH), 4.47 (s, 2H, CH$_2$), 3.66 (s, 2H, CH$_2$), 2.54 (d, J=7.0 Hz, 4H, CH$_2$), 1.02 (d, J=8.0 Hz, 12H, CH$_3$). R-MS (ESI): calcd. for C$_{24}$H$_{28}$N$_4$O$_2$ [M+H$^+$] 458.2729 found 458.4982.

Example 25

Synthesis of N-(2-((2-((diethylamino)methyl)benzyl)-3-(4-trifluoromethylbenzamide)benzamide With reference to the synthesis method of Example 1, the intermediate 1 in Example 1 was replaced with 3-(4-trifluoromethylbenzamido)benzoic acid to obtain a pale yellow solid compound, namely N-(2-((2-((diethylamino)methyl)benzyl)-3-(4-trifluoromethylbenzamide)benzamide (Compound 25). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 7.91 (q, $J_1$=1.5 Hz, $J_2$=1.5 Hz, $J_3$=7.5 Hz, 1H, ArH), 7.82 (dd, $J_1$=1.5 Hz, $J_2$=7.5 Hz, 2H, ArH), 7.79 (q, $J_1$=1.5 Hz, $J_2$=1.5 Hz, $J_3$=7.5 Hz, 1H, ArH), 7.65 (dd, $J_1$=1.5 Hz, $J_2$=7.5 Hz, 2H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for C$_{24}$H$_{28}$N$_4$O$_2$ [M+H$^+$] 484.2134 found 484.2134.

Example 26

Synthesis of N-(2-((2-((diethylamino)methyl)benzyl)-3-(4-methoxybenzamide)benzamide With reference to the synthesis method of Example 1, the intermediate 1 in Example 1 was replaced with 3-(4-methoxybenzamido)benzoic acid to obtain a pale yellow solid compound, namely N-(2-((2-((diethylamino)methyl)benzyl)-3-(4-methoxybenzamide)benzamide (Compound 26). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 7.96 (dd, $J_1$=1.5 Hz, $J_2$=7.5 Hz, 2H, ArH), 7.79 (q, $J_1$=1.5 Hz, $J_2$=1.5 Hz, $J_3$=7.5 Hz, 1H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 7.08 (dd, $J_1$=1.5 Hz, $J_2$=7.5 Hz, 2H, ArH), 4.47 (s, 2H, CH$_2$), 3.81 (s, 3H, CH$_3$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for $C_{24}H_{28}N_4O_2[M+H^+]$ 446.2365 found 446.2365.

Example 27

Synthesis of N-(2-((2-((diethylamino)methyl)benzyl)-3-(3-methoxybenzamide)benzamide With reference to the synthesis method of Example 1, the intermediate 1 in Example 1 was replaced with 3-(3-methoxybenzamido)benzoic acid to obtain a pale yellow solid compound, namely N-(2-((2-((diethylamino)methyl)benzyl)-3-(3-methoxybenzamide)benzamide (Compound 27). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 7.91 (q, $J_1$=1.5 Hz, $J_2$=1.5 Hz, $J_3$=7.5 Hz, 1H, ArH), 7.79 (q, $J_1$=1.5 Hz, $J_2$=1.5 Hz, $J_3$=7.5 Hz, 1H, ArH), 7.71 (t, J=7.5H, 1H, ArH), 7.63 (q, $J_1$=1.5 Hz, $J_2$=1.5 Hz, $J_3$=7.5 Hz, 1H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 7.19 (q, $J_1$=1.5 Hz, $J_2$=1.5 Hz, $J_3$=7.5 Hz, 1H, ArH), 6.77 (t, J=1.5H, 1H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for $C_{24}H_{28}N_4O_2[M+H^+]$ 446.2365 found 446.6379.

Example 28

Synthesis of N-(2-((2-((diethylamino)methyl)benzyl)-3-(2-methoxybenzamide)benzamide With reference to the synthesis method of Example 1, the intermediate 1 in Example 1 was replaced with 3-(2-methoxybenzamido)benzoic acid to obtain a pale yellow solid compound, namely N-(2-((2-((diethylamino)methyl)benzyl)-3-(2-methoxybenzamide)benzamide (Compound 28). There was one spot under TLC detection, there was a dark spot under ultraviolet light at 254 nm, and there was no fluorescence under 365 nm. $^1$H NMR (300 MHz, DMSO-d6): δ 10.32 (s, 1H, NHCO), 8.74 (s, 1H, NHCO), 8.13 (t, J=1.5H, 1H, ArH), 7.91 (q, $J_1$=1.5 Hz, $J_2$=1.5 Hz, $J_3$=7.5 Hz, 1H, ArH), 7.79 (q, $J_1$=1.5 Hz, $J_2$=1.5 Hz, $J_3$=7.5 Hz, 1H, ArH), 7.71 (t, J=7.5H, 1H, ArH), 7.64 (q, $J_1$=1.5 Hz, $J_2$=1.5 Hz, $J_3$=7.5 Hz, 1H, ArH), 7.57 (q, $J_1$=1.5 Hz, $J_2$=7.5 Hz, $J_3$=7.5 Hz, 1H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 7.23 (dd, $J_1$=1.5 Hz, $J_2$=7.5 Hz, 1H, ArH), 7.11 (q, $J_1$=1.5 Hz, $J_2$=7.5 Hz, $J_3$=7.5 Hz, 1H, ArH), 4.47 (s, 2H, CH$_2$), 3.93 (s, 3H, CH$_3$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for $C_{24}H_{28}N_4O_2[M+H^+]$ 446.2365 found 446.5206.

Example 29

Synthesis of methyl 4-((3-((2-((diethylamino)methyl)benzyl)carbamoyl)phenyl)carbamoyl)benzoate With reference to the synthesis method of Example 1, the intermediate 1 in Example 1 is replaced with 3-(4-(methoxycarbonyl)benzamido)benzoic acid to obtain a pale yellow solid compound, namely methyl 4-((3-((2-((diethylamino)methyl)benzyl)carbamoyl)phenyl)carbamoyl)benzoate (Compound 29). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 8.11 (dd, $J_1$=1.5 Hz, $J_2$=7.5 Hz, 2H, ArH), 7.91 (q, $J_1$=1.5 Hz, $J_2$=1.5 Hz, $J_3$=7.5 Hz, 1H, ArH), 7.90 (dd, $J_1$=1.5 Hz, $J_2$=7.5 Hz, 2H, ArH), 7.79 (q, $J_1$=1.5 Hz, $J_2$=1.5 Hz, $J_3$=7.5 Hz, 1H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 4.47 (s, 2H, CH$_2$), 3.89 (s, 3H, CH$_3$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for $C_{24}H_{28}N_4O_2$ $[M+H^+]$ 474.2315 found 474.3004.

Example 30

Synthesis of 3-(4-acetylbenzoyl)-N-(2-((diethylamino)methyl)benzyl)benzamide

With reference to the synthesis method of Example 1, the intermediate 1 in Example 1 was replaced with 3-(4-acetylbenzamido)benzoic acid to obtain a pale yellow solid compound, namely 3-(4-acetylbenzyl)-N-(2-((diethylamino)methyl)benzyl)benzamide (Compound 30). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 8.11 (dd, $J_1$=1.5 Hz, $J_2$=7.5 Hz, 2H, ArH), 8.08 (dd, $J_1$=1.5 Hz, $J_2$=7.5 Hz, 2H, ArH), 7.91 (q, $J_1$=1.5 Hz, $J_2$=1.5 Hz, $J_3$=7.5 Hz, 1H, ArH), 7.79 (q, $J_1$=1.5 Hz, $J_2$=1.5 Hz, $J_3$=7.5 Hz, 1H, ArH), 7.45 (t, J=1.5H, 1H, ArH), 7.43 (dd, $J_1$=1.5 Hz, $J_2$=7.5 Hz, 2H, ArH), 7.37 (q, $J_1$=1.5 Hz, $J_2$=1.5 Hz, $J_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for $C_{24}H_{28}N_4O_2[M+H^+]$ 458.2365 found 458.5092.

Example 31

Synthesis of 3-(4-cyanobenzamido)-N-(2-((diethylamino)methyl)benzyl)benzamide

With reference to the synthesis method of Example 1, the intermediate 1 in Example 1 was replaced with 3-(4-cyanobenzamido)benzoic acid to obtain a yellow oily liquid compound, namely 3-(4-cyanobenzamido)-N-(2-((diethylamino)methyl)benzyl)benzamide (Compound 31). There was one spot under TLC detection, there was a dark spot under ultraviolet light at 254 nm, and there was no fluorescence under 365 nm. $^1$H NMR (500 MHz, CDCl$_3$): δ 9.84 (s, 1H, CONH), 9.66 (s, 1H, CONH), 8.31 (d, J=7.8 Hz, 1H, ArH), 8.16 (s, 1H, ArH), 8.08 (d, J=8.2 Hz, 2H, ArH), 7.72 (d, J=8.2 Hz, 2H, ArH), 7.37 (t, J=7.8 Hz, 1H, ArH), 7.31 (d, J=7.8 Hz, 1H, ArH), 7.24 (td, J$_1$=8.8, J$_2$=4.9 Hz, 3H, ArH), 7.15 (m, 1H, ArH), 4.36 (d, J=5.0 Hz, 2H, CH$_2$), 3.61 (s, 2H, CH$_2$), 2.57 (q, J=7.1 Hz, 4H, CH$_2$), 0.99 (t, J=7.1 Hz, 6H, CH$_3$). MS (ESI): calcd. for C$_{27}$H$_{28}$N$_4$O$_2$[M+H]$^+$ 440.2212 found 440.3541.

Example 32

Synthesis of N-(2-((diethylamino)methyl)benzyl)-3-)4-nitrobenzamido)benzamide

With reference to the synthesis method of Example 1, the intermediate 1 in Example 1 was replaced with 3-(4-nitrobenzamido)benzoic acid to obtain a pale yellow solid compound, namely N-(2-((diethylamino)methyl)benzyl)-3-)4-nitrobenzamido)benzamide (Compound 32). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.39 (dd, J$_1$=1.5 Hz, J$_2$=7.5 Hz, 2H, ArH), 8.21 (dd, J$_1$=1.5 Hz, J$_2$=7.5 Hz, 2H, ArH), 8.13 (t, J=1.5H, 1H, ArH), 7.91 (q, J$_1$=1.5 Hz, J$_2$=1.5 Hz, J$_3$=7.5 Hz, 1H, ArH), 7.79 (q, J$_1$=1.5 Hz, J$_2$=1.5 Hz, J$_3$=7.5 Hz, 1H, ArH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=1.5 Hz, J$_3$=7.5 Hz, 2H, ArH), 4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for C$_{24}$H$_{28}$N$_4$O$_2$ [M+H$^+$] 461.2111 found 461.4013.

Example 33

Synthesis of N-(2-((diethylamino)methyl)benzyl)-3-)4-aminobenzamido)benzamide

With reference to the synthesis method of Example 1, the intermediate 1 in Example 1 was replaced with 3-(4-aminobenzamido)benzoic acid to obtain a pale yellow solid compound, namely N-(2-((diethylamino)methyl)benzyl)-3-)4-aminobenzamido)benzamide (Compound 33). There was one spot under TLC detection, there was a dark spot under ultraviolet light at 254 nm, and there was no fluorescence under 365 nm. $^1$H NMR (300 MHz, DMSO-d6): δ 10.40 (s, 1H, NHCO), 8.74 (s, 1H, NHCO), 8.13 (t, J=1.5H, 1H, ArH), 7.91 (q, J$_1$=1.5 Hz, J$_2$=1.5 Hz, J$_3$=7.5 Hz, 1H, ArH), 7.79 (q, J$_1$=1.5 Hz, J$_2$=1.5 Hz, J$_3$=7.5 Hz, 1H, ArH), 7.54 (dd, J$_1$=1.5 Hz, J$_2$=7.5 Hz, 2H, ArH), 7.45 (t, J=1.5H, 1H, ArH), 7.43 (dd, J$_1$=1.5 Hz, J$_2$=7.5 Hz, 2H, ArH), 7.37 (q, J$_1$=1.5 Hz, J$_2$=1.5 Hz, J$_3$=7.5 Hz, 2H, ArH), 6.54 (dd, J$_1$=1.5 Hz, J$_2$=7.5 Hz, 2H, ArH), 5.48 (s, 2H, NH$_2$)4.47 (s, 2H, CH$_2$), 3.66 (s, 2H, CH$_2$), 2.54 (d, J=7.0 Hz, 4H, CH$_2$), 1.02 (d, J=8.0 Hz, 6H, CH$_3$). R-MS (ESI): calcd. for C$_{24}$H$_{28}$N$_4$O$_2$ [M+H$^+$] 431.2369 found 431.3065. R-MS (ESI): calcd. for C$_{24}$H$_{28}$N$_4$O$_2$[M+H$^+$] 461.2111 found 461.4013.

Example 34

Synthesis of N-(3-((2-((dimethylamino)methyl)benzyl)carbamoyl)phenyl)thiophene-2-carboxamide With reference to the synthesis method of Example 1, the intermediate 2 in Example 1 was replaced with 1-2-(aminomethyl)phenyl)-N,N-dimethylmethylamine to obtain a yellow oily liquid compound, namely N-(3-((2-((dimethylamino)methyl)benzyl)carbamoyl)phenyl)thiophene-2-carboxamide (Compound 34). There was one spot under TLC detection, there was a dark spot under ultraviolet light at 254 nm, and there was no fluorescence under 365 nm. $^1$H NMR (500 MHz, CDCl$_3$): δ 9.94 (s, 1H, CONH), 8.84 (s, 1H, CONH), 8.09 (d, J=8.0 Hz, 1H, ArH), 8.05 (s, 1H, ArH), 7.82 (d, J=3.5 Hz, 1H, ArH), 7.55 (d, J=4.5 Hz, 1H, ArH), 7.37 (d, J=4.5 Hz, 1H, ArH), 7.34 (dd, J$_1$=8.0, J$_2$=3.5 Hz, 2H, ArH), 7.26 (m, 2H, ArH), 7.22 (m, 1H, ArH), 7.12 (t, J=4.5 Hz, 1H, ArH), 4.59 (d, J=4.5 Hz, 2H, CH$_2$), 3.50 (s, 2H, CH$_2$), 2.28 (s, 6H, CH$_3$). MS (ESI): calcd. for C$_{22}$H$_{23}$N$_3$O$_2$S[M+H]$^+$ 394.1511 found 394.4213.

Example 35

Synthesis of N-(3-((2-((dipropylamino)methyl)benzyl)carbamoyl)phenyl)thiophene-2-carboxamide With reference to the synthesis method of Example 1, the intermediate 2 in Example 1 was replaced with 1-2-(aminomethyl)phenyl)-N,N-dipropylmethylamine to obtain a yellow oily liquid compound, namely N-(3-((2-((dipropylamino)methyl)benzyl)carbamoyl)phenyl)thiophene-2-carboxamide (Compound 35). There was one spot under TLC detection, there was a dark spot under ultraviolet light at 254 nm, and there was no fluorescence under 365 nm. $^1$H NMR (500 MHz, CDCl$_3$): δ 9.22 (s, 1H, CONH), 8.50 (s, 1H, CONH), 8.13 (d, J=7.5 Hz, 1H, ArH), 7.96 (s, 1H, ArH), 7.77 (d, J=3.5 Hz, 1H, ArH), 7.56 (d, J=5.0 Hz, 1H, ArH), 7.41 (q, J=8.0 Hz, 2H, ArH), 7.37 (t, J=8.0 Hz, 1H, ArH), 7.30 (m, 1H, ArH), 7.25 (t, J=8.0 Hz, 2H, ArH), 7.13(t, J=4.0 Hz, 1H, ArH), 4.62 (s, 2H, CH$_2$), 3.69 (s, 2H, CH$_2$), 2.48 (t, J=7.5 Hz, 4H, CH$_2$), 1.49 (tt, J=15.0, 7.5 Hz, 4H, CH$_2$), 0.80 (t, J=7.5 Hz, 6H, CH$_3$). MS (ESI): calcd. for C$_{26}$H$_{31}$N$_3$O$_2$S [M+H]$^+$ 450.2137 found 450.4125.

Example 36

Synthesis of N-(3-(benzylamino)phenyl)thiophene-2-carboxamide

With reference to the synthesis method of Example 1, the intermediate 2 in Example 1 was replaced with benzylamine to obtain a white solid compound, namely N-(3-(benzylamino)phenyl)thiophene-2-carboxamide (Compound 36). There was one spot under TLC detection, there was a dark spot under ultraviolet light at 254 nm, and there was no fluorescence under 365 nm. $^1$H NMR (500 MHz, DMSO): δ 10.39 (s, 1H, CONH), 9.05 (t, J=5.5 Hz, 1H, CONH), 8.21 (s, 1H, ArH), 8.07 (m, 1H, ArH), 7.95 (dd, J$_1$=8.0, J$_2$=1.0 Hz, 1H, ArH), 7.88 (d, J=5.0 Hz, 1H, ArH), 7.64 (d, J=7.5 Hz, 1H, ArH), 7.46 (t, J=8.0 Hz, 1H, ArH), 7.34 (s, 2H, ArH), 7.34 (s, 2H, ArH), 7.25 (m, J=9.0, 2H, ArH), 4.50 (d, J=6.0 Hz, 2H, CH$_2$). MS (ESI): calcd. for C$_{19}$H$_{16}$N$_2$O$_2$S [M+H]$^+$ 337.0932 found 337.1254.

Example 37

Synthesis of N-(3-((3-((diethylamino)methyl)benzyl)carbamoyl)phenyl)thiophene-2-carboxamide With reference to the synthesis method of Example 1, the intermediate 2 in Example 1 was replaced with N-(3-(aminomethyl)benzyl)-N-ethylethylamine to obtain a pale yellow solid compound, namely N-(3-((3-((diethylamino)methyl)benzyl)carbamoyl)phenyl)thiophene-2-carboxamide (Compound 37). There was one spot under TLC detection, there was a dark spot under ultraviolet light at 254 nm, and there was no fluorescence under 365 nm. $^1$H NMR (300

MHz, DMSO-d6): δ 10.20 (s, 1H, NHCO), 8.92 (s, 1H, NHCO), 8.30 (dd, $J_1$=1.5 Hz, $J_2$=7.5 Hz, 1H, ArH), 8.13 (t, J=1.5H, 1H, ArH), 7.98 (dd, $J_1$=1.5 Hz, $J_2$=7.5 Hz, 1H, ArH), 7.91 (q, $J_1$=1.5 Hz, $J_2$=1.5 Hz, $J_3$=7.5 Hz, 1H, ArH), 7.79 (q, $J_1$=1.5 Hz, $J_2$=1.5 Hz, $J_3$=7.5 Hz, 1H, ArH), 7.59 (t, J=7.5H, 1 Hz, ArH), 7.45 (t, J=7.5 Hz, 1H, ArH), 7.31 (t, J=1.5H, 1 Hz, ArH), 7.28 (q, $J_1$=1.5 Hz, $J_2$=1.5 Hz, $J_3$=7.5 Hz, 2H, ArH), 7.20 (t, J=7.5H, 1 Hz, ArH), 4.47 (s, 2H, $CH_2$), 3.66 (s, 2H, $CH_2$), 2.56 (d, J=8.0 Hz, 4H, $CH_2$), 1.02 (d, J=8.0 Hz, 6H, $CH_3$). R-MS (ESI): calcd. for $C_{24}H_{28}N_4O_2$ [M+H$^+$] 422.1824 found 422.2948.

Example 38

Synthesis of N-(3-((4-((diethylamino)methyl)benzyl)carbamoyl)phenyl)thiophene-2-carboxamide With reference to the synthesis method of Example 1, the intermediate 2 in Example 1 was replaced with N-(4-(aminomethyl)benzyl)-N-ethylethylamine to obtain a pale yellow solid compound, namely N-(3-((4-((diethylamino)methyl)benzyl)carbamoyl)phenyl)thiophene-2-carboxamide (Compound 37). There was one spot under TLC detection, there was a dark spot under ultraviolet light at 254 nm, and there was no fluorescence under 365 nm. $^1$H NMR (300 MHz, DMSO-d6): δ 10.20 (s, 1H, NHCO), 8.92 (s, 1H, NHCO), 8.30 (dd, $J_1$=1.5 Hz, $J_2$=7.5 Hz, 1H, ArH), 8.13 (t, J=1.5H, 1H, ArH), 7.98 (dd, $J_1$=1.5 Hz, $J_2$=7.5 Hz, 1H, ArH), 7.91 (q, $J_1$=1.5 Hz, $J_2$=1.5 Hz, $J_3$=7.5 Hz, 1H, ArH), 7.79 (q, $J_1$=1.5 Hz, $J_2$=1.5 Hz, $J_3$=7.5 Hz, 1H, ArH), 7.45 (t, J=7.5 Hz, 1H, ArH), 7.27 (dd, $J_1$=1.5 Hz, $J_2$=7.5 Hz, 4H, ArH), 7.20 (t, J=7.5H, 1 Hz, ArH), 4.47 (s, 2H, $CH_2$), 3.66 (s, 2H, $CH_2$), 2.56 (d, J=8.0 Hz, 4H, $CH_2$), 1.02 (d, J=8.0 Hz, 6H, $CH_3$). R-MS (ESI): calcd. for $C_{24}H_{28}N_4O_2$[M+H$^+$] 422.1824 found 422.7979.

The following are the pharmacodynamic tests and results of some compounds of the present invention:

Determination of Cholinesterase Inhibitory Activity:

Drugs and reagents: Test compounds, AChE (E.C.3.1.1.7, Type VI-S, selected from electric eel), BuChE (E.C.3.1.1.8, selected from horse serum), 5,5'-dithiobis(2-nitrobenzoic acid) (DTNB), acetylthiocholine (ATC) iodide and butyrylthiocholine (BTC) iodide were all purchased from Sigma; the positive control tacrine hydrochloride (9-amino-1,2,3,4-tetrahydroacridine hydrochloride hydrate) was purchased from BioTrend.

Instrument: THERMO Varioskan Flash full-wavelength multifunctional microplate reader.

Experimental Method:
(1) Formulation of buffer: 13.6 g of potassium dihydrogen phosphate was dissolved in 1 L of water, and pH was adjusted with potassium hydroxide to reach pH=8±0.1. The solution was stored at 4° C. for later use.
(2) Formulation of 0.01 M DTNB solution: 0.396 g of DTNB and 0.15 g of sodium bicarbonate were dissolved in 100 mL of water to prepare a 0.01 M DTNB solution, which was stored at −30° C. for later use.
(3) Formulation of 0.075 M ATC and BTC solutions: 0.217 g of ATC was dissolved in 10 mL of water to prepare a 0.075 M ATC solution, which was stored at −30° C. for later use; 0.237 g of BTC was dissolved in 10 mL of water to prepare a 0.075 M BTC solution, which was stored at −30° C. for later use.
(4) Formulation of AChE and BuChE solutions: 5,000 units of AChE were dissolved in 1 mL of 1% gel solution, and then diluted to 100 mL with water to prepare a AChE solution with a concentration of 5 units/mL, which was stored at −30° C. for later use; 5,000 units of BuChE were dissolved in 1 mL of 1% gel solution, and then diluted to 100 mL with water to prepare a BuChE solution with a concentration of 5 units/mL, which was stored at −30° C. for later use.
(5) Formulation of test substance solution: The test compound was dissolved in ethanol to obtain a solution with a concentration of $10^{-3}$ M (ethanol would not affect the test results), and then diluted with water to prepare solutions with concentrations of $10^{-1}$, $10^{-5}$, $10^{-6}$, $10^{-7}$, $10^{-8}$, $10^{-9}$, and $10^{-10}$ M, respectively.

Before the start of the experiment, all the solutions as used were warmed to room temperature, and the AChE and BuChE solutions were diluted 1-fold with water to prepare an enzyme solution with a concentration of 2.5 units/mL. The background UV absorbance was measured with a blank buffer (3 mL) as a subtraction value. Firstly, 100 μL of test compound solution, 100 μL of DTNB solution, and 100 μL of enzyme solution were added to 3 mL of buffer. After adding 20 μL of ATC or BTC solution to trigger the reaction, the time was recorded immediately and the test solution was mixted quickly and uniformly at the same time. After 2 minutes, the UV absorbance was measured at a wavelength of 412 m. The blank control group was measured with an equal volume of water instead of the test substance solution. All tests were performed three times in parallel. The UV absorption value of the blank control group was taken as 100%, the absorbance (OD value) of the test compound at each concentration was recorded, and GraphPad Prism™ (GraphPad Software, San Diego, CA, USA) software was used to analyze the results in a non-linear regression analysis model to calculate the corresponding $IC_{50}$ values, as shown in Table 1.

TABLE 1

Test results of each compound on eqBuChE and hBuChE

| Compound | Structural formula | $IC_{50}$ (nM) ± SEM | |
| --- | --- | --- | --- |
| | | eqBuChE | hBuChE |
| N-(3-((2-((diethylamino)methyl)benzyl)carbamoyl)phenyl)thiophene-2-carboxamide | | 0.13 ± 0.01 | 0.42 ± 0.07 |

TABLE 1-continued

Test results of each compound on eqBuChE and hBuChE

| Compound | Structural formula | IC$_{50}$ (nM) ± SEM | |
| --- | --- | --- | --- |
| | | eqBuChE | hBuChE |
| N-(3-((2-((dimethylamino)methyl)phenyl)carbamoyl)phenyl)thiophene-2-carboxamide | 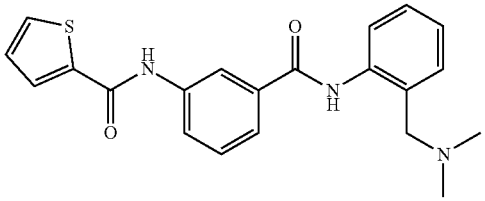 [SMILES: CN(C)Cc1ccccc1NC(=O)c1cccc(NC(=O)c2cccs2)c1] | 1906.00 ± 983.00 | ND |
| N-(3-((2-((diethylamino)methyl)phenyl)carbamoyl)phenyl)thiophene-2-carboxamide | 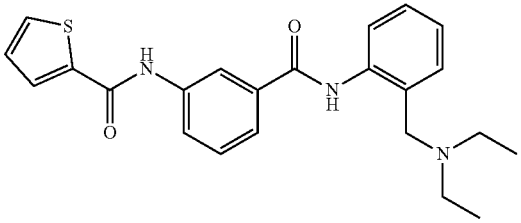 [SMILES: CCN(CC)Cc1ccccc1NC(=O)c1cccc(NC(=O)c2cccs2)c1] | 480.80 ± 109.55 | ND |
| N-(3-((2-((dipropylamino)methyl)phenyl)carbamoyl)phenyl)thiophene-2-carboxamide | 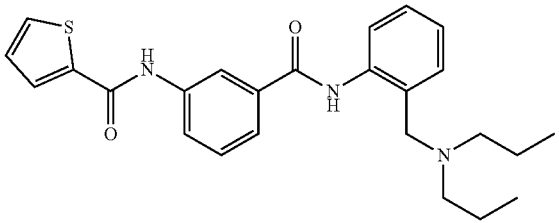 [SMILES: CCCN(CCC)Cc1ccccc1NC(=O)c1cccc(NC(=O)c2cccs2)c1] | 122.200 ± 284.7 | ND |
| N-(3-((2-((diethylamino)methyl)benzyl)carbamoyl)phenyl)-pyrrole-2-carboxamide | 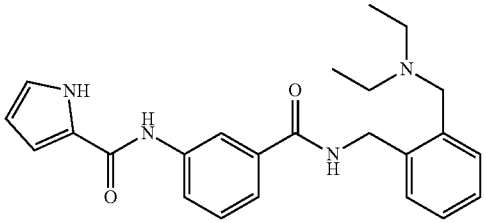 [SMILES: CCN(CC)Cc1ccccc1CNC(=O)c1cccc(NC(=O)c2ccc[nH]2)c1] | 0.87 ± 0.03 | 2.99 ± 0.67 |
| N-(3-((2-((diethylamino)methyl)benzyl)carbamoyl)phenyl)furan-2-carboxamide | 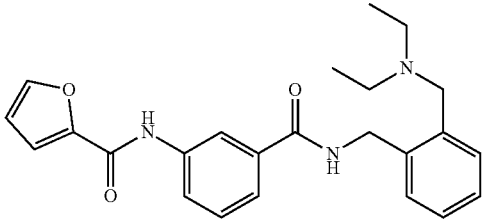 [SMILES: CCN(CC)Cc1ccccc1CNC(=O)c1cccc(NC(=O)c2ccco2)c1] | 0.79 ± 0.09 | 0.63 ± 0.13 |
| N-(3-((2-((diethylamino)methyl)benzyl)carbamoyl)phenyl)-pyridine-2-carboxamide | 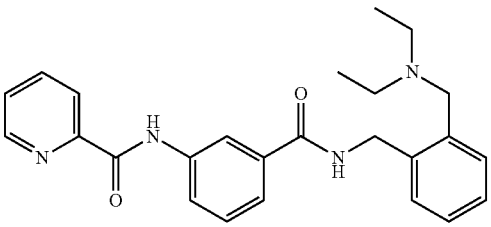 [SMILES: CCN(CC)Cc1ccccc1CNC(=O)c1cccc(NC(=O)c2ccccn2)c1] | 0.34 ± 0.02 | 0.78 ± 0.63 |

TABLE 1-continued

Test results of each compound on eqBuChE and hBuChE

| Compound | Structural formula | IC$_{50}$ (nM) ± SEM | |
|---|---|---|---|
| | | eqBuChE | hBuChE |
| N-(3-((2-((diethylamino)methyl)benzyl)carbamoyl)phenyl)-thiazole-2-carboxamide | | 0.75 ± 0.14 | 1.88 ± 0.52 |
| N-(3-((2-((diethylamino)methyl)benzyl)carbamoyl)phenyl)-imidazole-2-carboxamide | | 0.52 ± 0.10 | 1.91 ± 0.24 |
| 3-(cyclohexanecarboxamido)-N-(2-((diethylamino)methyl)benzyl)benzamide | | 121.98 ± 15.39 | ND |
| 3-benzamido-N-(2-((diethylamino)methyl)benzyl)benzamide | | 0.48 ± 0.07 | 0.99 ± 0.18 |
| N-(2-((diethylamino)methyl)benzyl)-3-(4-hydroxybenzamido)benzamide | | 0.79 ± 0.19 | 2.45 ± 0.37 |
| 4-((3-((2-((diethylamino)methyl)benzyl)carbamoyl)phenyl)carbamoyl)benzoic acid | | 0.76 ± 0.09 | 3.40 ± 0.31 |

TABLE 1-continued

Test results of each compound on eqBuChE and hBuChE

| Compound | Structural formula | IC$_{50}$ (nM) ± SEM | |
|---|---|---|---|
| | | eqBuChE | hBuChE |
| N-(2-((diethylamino)methyl)benzyl)-3-(4-formanilide)benzamide | | 0.89 ± 0.63 | 2.09 ± 0.99 |
| N-(2-((diethylamino)methyl)benzyl)-3-(4-fluorobenzamido)benzamide | | 0.15 ± 0.06 | 1.44 ± 1.66 |
| N-(3-((2-(diethylamino)methyl)benzyl)carbamoyl)phenyl)-3,4-difluorobenzamide | | 0.30 ± 0.07 | 0.57 ± 0.10 |
| N-(2-((diethylamino)methyl)benzyl)-3-(3-fluorobenzamido)benzamide | | 4.55 ± 0.74 | 25.19 ± 19.07 |
| N-(3-((2-((diethylamino)methyl)benzyl)carbamoyl)phenyl)-2-fluorobenzamide | | 3.50 ± 1.10 | 17.36 ± 1.98 |
| 3-(4-chlorobenzamido)-N-(2-((diethylamino)methyl)benzyl)benzamide | | 0.34 ± 0.21 | 0.83 ± 0.39 |

TABLE 1-continued

Test results of each compound on eqBuChE and hBuChE

| Compound | Structural formula | IC$_{50}$ (nM) ± SEM | |
| --- | --- | --- | --- |
| | | eqBuChE | hBuChE |
| 3-(4-bromobenzamido)-N-(2-((diethylamino)methyl)benzyl)benzamide | | 0.98 ± 0.62 | 1.91 ± 0.59 |
| 3-(4-iodobenzamido)-N-(2-((diethylamino)methyl)benzyl)benzamide | | 1.59 ± 0.26 | 3.33 ± 1.62 |
| N-(2-((diethylamino)methyl)benzyl)-3-(4-methylbenzamido)benzamide | | 0.98 ± 0.21 | 1.54 ± 0.56 |
| N-(3-((2-((diethylamino)methyl)benzyl)carbamoyl)phenyl)-3,4-dimethylbenzamide | | 0.80 ± 0.24 | 1.53 ± 0.55 |
| N-(2-((2-((diethylamino)methyl)benzyl)-3-(4-isopropylbenzamide)benzamide | | 0.58 ± 0.67 | 2.08 ± 0.73 |
| N-(2-((2-((diethylamino)methyl)benzyl)-3-(4-trifluoromethylbenzamide)benzamide | | 0.38 ± 0.10 | 1.41 ± 0.01 |

TABLE 1-continued

Test results of each compound on eqBuChE and hBuChE

| Compound | Structural formula | IC$_{50}$ (nM) ± SEM | |
| --- | --- | --- | --- |
| | | eqBuChE | hBuChE |
| N-(2-((2-((diethylamino)methyl)benzyl)-3-(4-methoxybenzamide)benzamide | 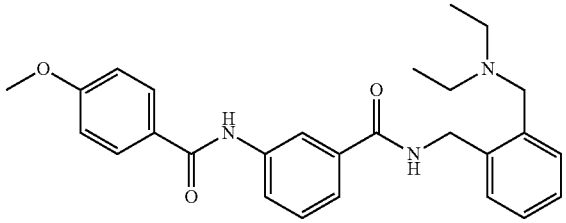 [SMILES: CCN(CC)Cc1ccccc1CNC(=O)c1cccc(NC(=O)c2ccc(OC)cc2)c1] | 0.55 ± 0.09 | 1.04 ± 0.52 |
| N-(2-((2-((diethylamino)methyl)benzyl)-3-(3-methoxybenzamide)benzamide | 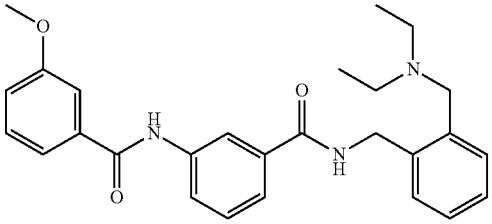 [SMILES: CCN(CC)Cc1ccccc1CNC(=O)c1cccc(NC(=O)c2cccc(OC)c2)c1] | 4.91 ± 1.35 | 12.85 ± 6.01 |
| N-(2-((2-((diethylamino)methyl)benzyl)-3-(2-methoxybenzamide)benzamide | 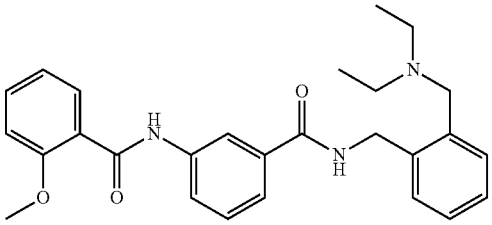 [SMILES: CCN(CC)Cc1ccccc1CNC(=O)c1cccc(NC(=O)c2ccccc2OC)c1] | 5.28 ± 1.21 | 19.98 ± 2.06 |
| Methyl 4-((3-((2-((diethylamino)methyl)benzyl)carbamoyl)phenyl)carbamoyl)benzoate | 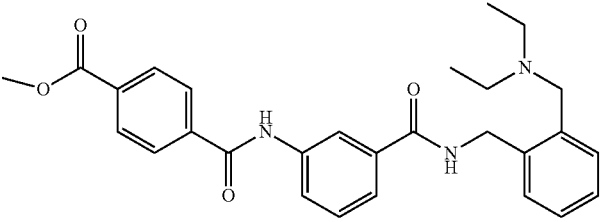 [SMILES: CCN(CC)Cc1ccccc1CNC(=O)c1cccc(NC(=O)c2ccc(C(=O)OC)cc2)c1] | 2.48 ± 0.26 | 9.06 ± 0.74 |
| 3-(4-acetylbenzoyl)-N-(2-((diethylamino)methyl)benzyl)benzamide | 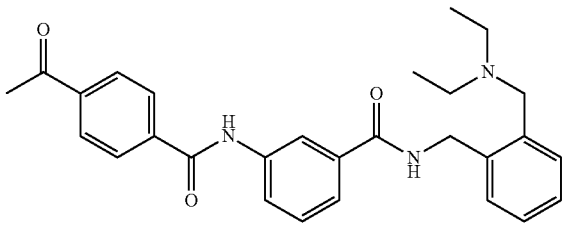 [SMILES: CCN(CC)Cc1ccccc1CNC(=O)c1cccc(NC(=O)c2ccc(C(C)=O)cc2)c1] | 6.63 ± 0.66 | 23.98 ± 1.52 |
| 3-(4-cyanobenzamido)-N-(2-((diethylamino)methyl)benzyl)benzamide | 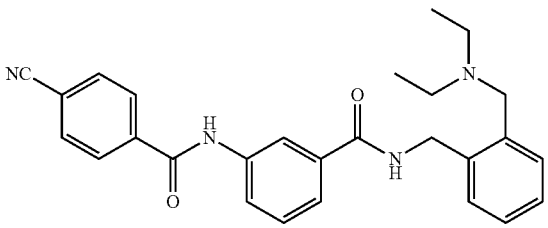 [SMILES: CCN(CC)Cc1ccccc1CNC(=O)c1cccc(NC(=O)c2ccc(C#N)cc2)c1] | 15.78 ± 2.84 | 16.54 ± 15.11 |

TABLE 1-continued

Test results of each compound on eqBuChE and hBuChE

| Compound | Structural formula | IC$_{50}$ (nM) ± SEM | |
|---|---|---|---|
| | | eqBuChE | hBuChE |
| N-(2-((diethylamino)methyl)benzyl)-3-)4-nitrobenzamido)benzamide | | 22.65 ± 0.98 | 30.90 ± 3.26 |
| N-(2-((diethylamino)methyl)benzyl)-3-)4-aminobenzamido)benzamide | | 1.56 ± 0.67 | 7.99 ± 2.53 |
| N-(3-((2-((dimethylamino)methyl)benzyl)carbamoyl)phenyl)thiophene-2-carboxamide | | 0.29 ± 0.05 | 0.75 ± 0.27 |
| N-(3-((2-((dipropylamino)methyl)benzyl)carbamoyl)phenyl)thiophene-2-carboxamide | | 0.45 ± 0.04 | 0.89 ± 0.67 |
| N-(3-(benzylamino)phenyl)thiophene-2-carboxamide | | 27.23%[a] | ND |
| N-(3-((3-((diethylamino)methyl)benzyl)carbamoyl)phenyl)thiophene-2-carboxamide | | 12.56 ± 0.86 | 32.87 ± 15.66 |
| N-(3-((4-((diethylamino)methyl)benzyl)carbamoyl)phenyl)thiophene-2-carboxamide | | 24.68 ± 10.63 | 75.05 ± 22.87 |

[a] represents the inhibition rate of the compound on the target at a concentration of 10 μM The 38 compounds in Table 1 all show better inhibitory activity on BuChE (the best compound is compound 1, and its BuChE inhibitory activity is 0.13±0.01 nM), and all have no inhibitory activity on AChE at a concentration of 10 M (the inhibition rate at a concentration of 10 M is less than 10%), indicating that this series of compounds have extremely high selectivity. In a healthy brain, the activity of AChE is dominant (80%), while BuChE appears to only play a supporting role. However, in progressive AD, the levels of AChE in the brain gradually decrease to 55-67% of normal level, while the levels of BuChE increase to 120% of normal level. This suggests that in the middle and late stages of severe AD, BuChE replaces the dominating role of AChE and becomes the main metabolic enzyme for hydrolyzing Ach, which deserves more attention. However, selective BuChE inhibitors show weak peripheral cholinergic side effects during the treatment process and have stronger drug safety. Therefore, the development of selective BuChE inhibitors is of great significance. The compound involved in the present invention has good inhibitory activity and extremely high selectivity to BuChE, and is expected to have a good curative effect on AD.

Toxicity Test in PC-12 Nerve Cell:

Drugs and reagents: Test compounds, DMEM medium (01-050-1A) purchased from Biological Industries, FBS fetal bovine serum (04-001-1A) purchased from Biological Industries, MTT thiazolyl blue reagent (KGT525500) purchased from KeyGEN BioTECH.

Instrument: THERMO Varioskan Flash full-wavelength multifunctional microplate reader.

Experimental Method:

About $3\times10^3$ PC-12 cells were evenly mixed in 0.1 mL of DMEM medium containing 10% FBS, and plated on a 96-well bottom plate, and incubated overnight at 37° C. in an environment containing 5% $CO_2$. The 20 μM and 50 μM compounds diluted in 0.1 mL of DMEM medium were treated on the cells for 24 hours. Then MTT reagent was added to the well plate, and the plate was incubated at 37° C. for 2 to 4 hours. The color reaction was measured at 492 nm using a spectrophotometer (Thermo, multiskan FC). The cell survival rate (SR %) corresponding to the compound represented by formula (I) was calculated, as shown in Table 2.

TABLE 2

Survival rate test results of each compound on PC-12 neural cell line

| Compound | 20 μM SR(%)[a] | 50 μM SR(%)[b] |
| --- | --- | --- |
| N-(3-((2-((diethylamino)methyl)benzyl)carbamoyl)phenyl)thiophene-2-carboxamide | 97.36 | 84.34 |
| N-(3-((2-((dimethylamino)methyl)phenyl)carbamoyl)phenyl)thiophene-2-carboxamide | 94.30 | 91.45 |
| N-(3-((2-((diethylamino)methyl)phenyl)carbamoyl)phenyl)thiophene-2-carboxamide | 95.23 | 89.64 |
| N-(3-((2-((dipropylamino)methyl)phenyl)carbamoyl)phenyl)thiophene-2-carboxamide | 87.24 | 79.48 |
| N-(3-((2-((diethylamino)methyl)benzyl)carbamoyl)phenyl)-pyrrole-2-carboxamide | 97.53 | 92.47 |
| N-(3-((2-((diethylamino)methyl)benzyl)carbamoyl)phenyl)furan-2-carboxamide | 95.37 | 81.46 |
| N-(3-((2-((diethylamino)methyl)benzyl)carbamoyl)phenyl)-pyridine-2-carboxamide | 92.36 | 75.46 |
| N-(3-((2-((diethylamino)methyl)benzyl)carbamoyl)phenyl)-thiazole-2-carboxamide | 93.57 | 89.42 |
| N-(3-((2-((diethylamino)methyl)benzyl)carbamoyl)phenyl)-imidazole-2-carboxamide | 80.36 | 70.74 |
| 3-(cyclohexanecarboxamido)-N-(2-((diethylamino)methyl)benzyl)benzamide | 90.23 | 83.22 |
| 3-benzamido-N-(2-((diethylamino)methyl)benzyl)benzamide | 96.30 | 83.4 |
| N-(2-((diethylamino)methyl)benzyl)-3-(4-hydroxybenzamido)benzamide | 91.46 | 89.64 |
| 4-((3-((2-((diethylamino)methyl)benzyl)carbamoyl)phenyl)carbamoyl)benzoic acid | 91.46 | 75.25 |
| N-(2-((diethylamino)methyl)benzyl)-3-(4-formanilide)benzamide | 86.34 | 81.34 |
| N-(2-((diethylamino)methyl)benzyl)-3-(4-fluorobenzamido)benzamide | 93.57 | 84.35 |
| N-(3-((2-(diethylamino)methyl)benzyl)carbamoyl)phenyl)-3,4-difluorobenzamide | 95.72 | 89.53 |
| N-(2-((diethylamino)methyl)benzyl)-3-(3-fluorobenzamido)benzamide | 98.40 | 89.75 |
| N-(3-((2-((diethylamino)methyl)benzyl)carbamoyl)phenyl)-2-fluorobenzamide | 80.26 | 73.56 |
| 3-(4-chlorobenzamido)-N-(2-((diethylamino)methyl)benzyl)benzamide | 90.43 | 79.24 |
| 3-(4-bromobenzamido)-N-(2-((diethylamino)methyl)benzyl)benzamide | 94.00 | 85.21 |
| 3-(4-iodobenzamido)-N-(2-((diethylamino)methyl)benzyl)benzamide | 94.40 | 89.63 |
| N-(2-((diethylamino)methyl)benzyl)-3-(4-methylbenzamido)benzamide | 93.35 | 89.42 |
| N-(3-((2-((diethylamino)methyl)benzyl)carbamoyl)phenyl)-3,4-dimethylbenzamide | 85.05 | 80.72 |
| N-(2-((2-((diethylamino)methyl)benzyl)-3-(4-isopropylbenzamide)benzamide | 97.02 | 86.21 |
| N-(2-((2-((diethylamino)methyl)benzyl)-3-(4-trifluoromethylbenzamide)benzamide | 97.58 | 91.57 |
| N-(2-((2-((diethylamino)methyl)benzyl)-3-(4-methoxybenzamide)benzamide | 97.20 | 82.25 |
| N-(2-((2-((diethylamino)methyl)benzyl)-3-(3-methoxybenzamide)benzamide | 91.23 | 83.60 |
| N-(2-((2-((diethylamino)methyl)benzyl)-3-(2-methoxybenzamide)benzamide | 95.42 | 85.46 |
| Methyl 4-((3-((2-((diethylamino)methyl)benzyl)carbamoyl)phenyl)carbamoyl)benzoate | 99.42 | 93.32 |
| 3-(4-acetylbenzoyl)-N-(2-((diethylamino)methyl)benzyl)benzamide | 91.86 | 72.56 |
| 3-(4-cyanobenzamido)-N-(2-((diethylamino)methyl)benzyl)benzamide | 94.67 | 91.59 |
| N-(2-((diethylamino)methyl)benzyl)-3-)4-nitrobenzamido)benzamide | 97.42 | 84.65 |
| N-(2-((diethylamino)methyl)benzyl)-3-)4-aminobenzamido)benzamide | 90.21 | 74.62 |
| N-(3-((2-((dimethylamino)methyl)benzyl)carbamoyl)phenyl)thiophene-2-carboxamide | 96.10 | 94.5 |
| N-(3-((2-((dipropylamino)methyl)benzyl)carbamoyl)phenyl)thiophene-2-carboxamide | 92.58 | 84.86 |
| N-(3-(benzylamino)phenyl)thiophene-2-carboxamide | 89.57 | 77.42 |
| N-(3-((3-((diethylamino)methyl)benzyl)carbamoyl)phenyl)thiophene-2-carboxamide | 92.05 | 82.03 |
| N-(3-((4-((diethylamino)methyl)benzyl)carbamoyl)phenyl)thiophene-2-carboxamide | 93.67 | 84.23 |

[a]Cell survival rate (SR %) after treatment with 20 μM compound for 24 h
[b]Cell survival rate (SR %) after treatment with 50 μM compound for 24 h The 38 compounds in Table 1 are less toxic to PC-12 nerve cells at the two concentrations of 20 M and 50 μM, indicating that they have good drug safety in vitro and lay a foundation for its subsequent development as selective BuChE inhibitors for the treatment of AD.

What is claimed is:

1. A selective butyrylcholinesterase inhibitor having a general formula (I) or a pharmaceutically acceptable salt thereof,

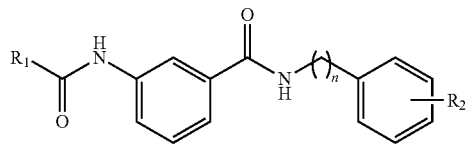

(I)

wherein n is an integer from 0 to 3;
$R_1$ represents

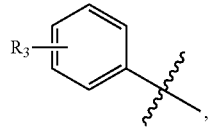

furan, pyrrole, pyridine, thiazole, imidazole or cyclohexane;
wherein $R_3$ represents hydroxyl, $C_1$-$C_4$ carboxyl, $C_1$-$C_4$ aldehyde group, chlorine, bromine, iodine, $C_1$-$C_4$ alkyl, halogen-substituted $C_1$-$C_4$ alkyl, $C_1$-$C_4$ alkoxy, $C_1$-$C_4$ alkoxycarbonyl, $C_1$-$C_4$ acyl, cyano, nitro or —$NR_5R_6$, where $R_5$ and $R_6$ represent $C_1$-$C_3$ alkyl;
$R_2$ represents —$CH_2N(CH_3)_2$ or —$CH_2N(C_3H_7)_2$;
wherein the selective butyrylcholinesterase inhibitor is selected from the group consisting of:

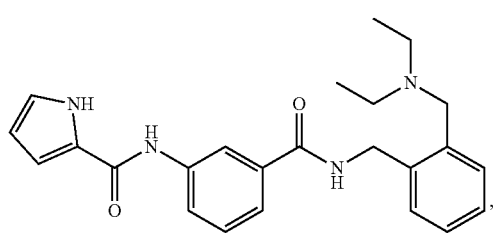

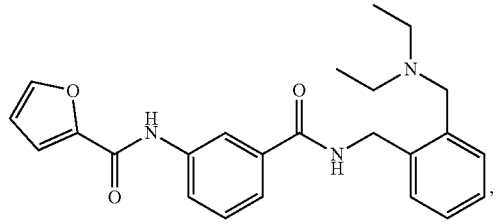

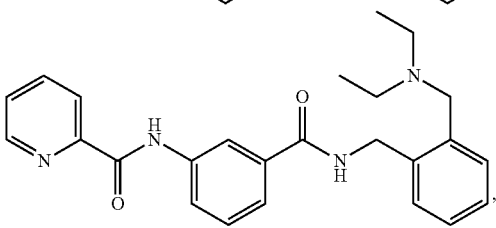

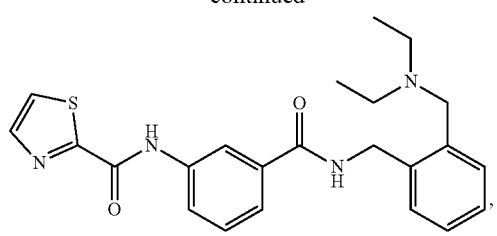

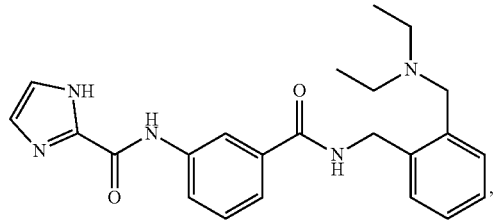

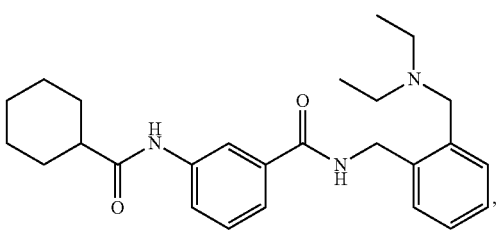

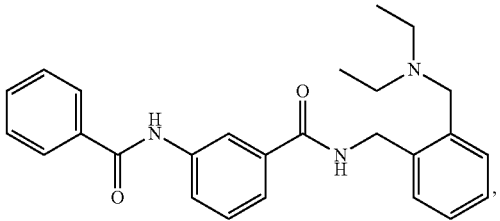

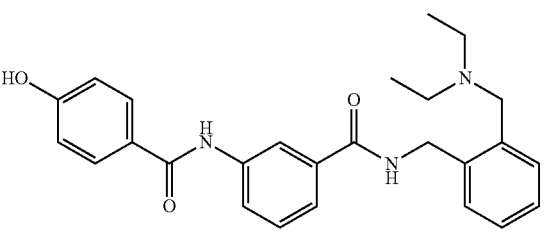

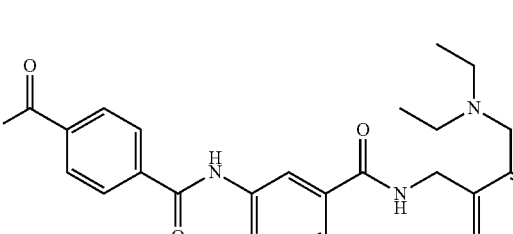

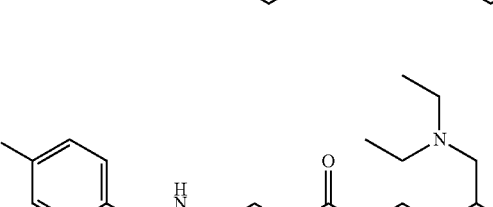

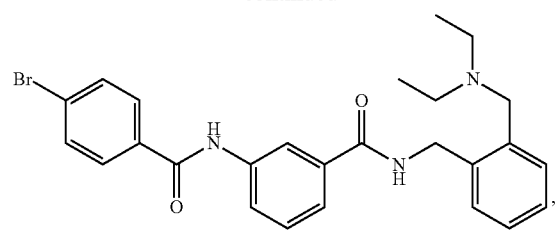,

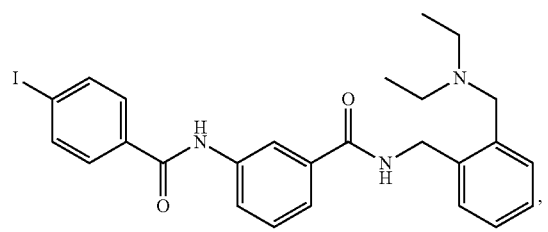,

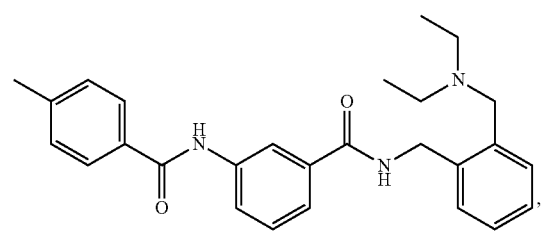,

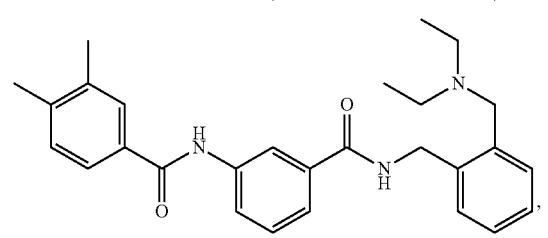,

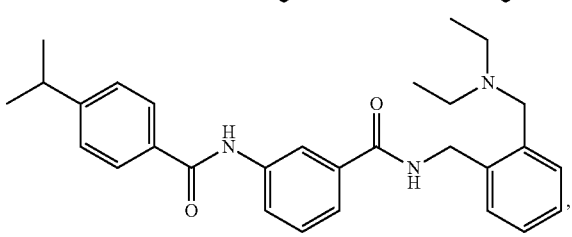,

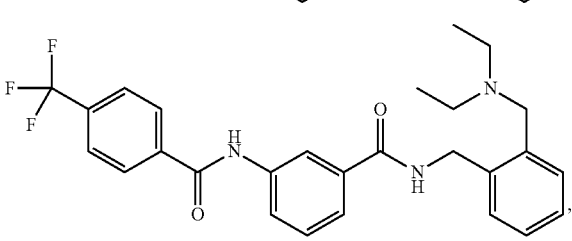,

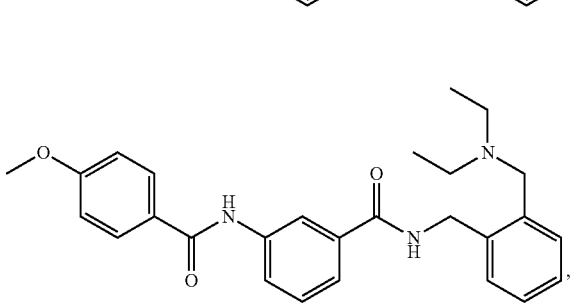,

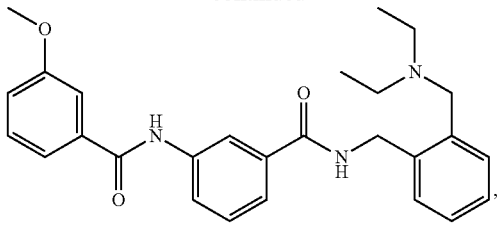,

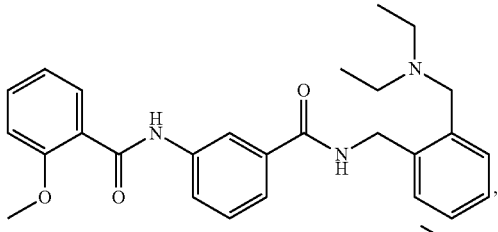,

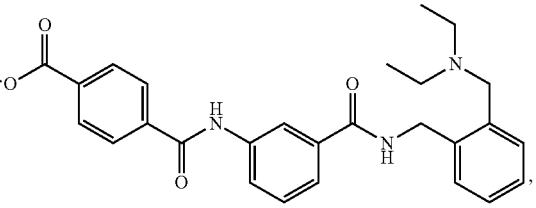,

,

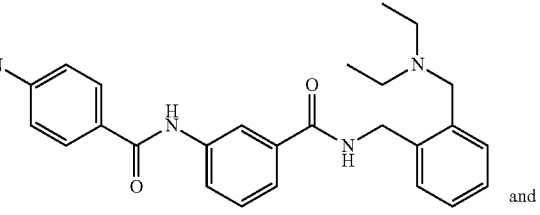

and

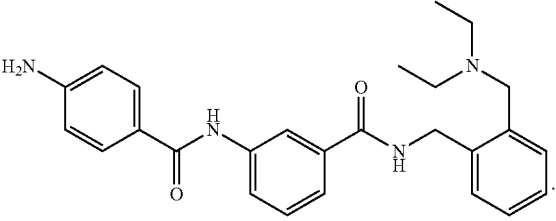.

2. A pharmaceutical composition containing a therapeutically effective amount of one or more selective butyrylcholinesterase inhibitors or a pharmaceutically acceptable salt thereof according to claim 1 and a pharmaceutically acceptable carrier.

3. The pharmaceutical composition according to claim 2, wherein the pharmaceutical composition further contains a pharmaceutically acceptable auxiliary material.

4. The pharmaceutical composition according to claim 2, wherein the pharmaceutical composition is a tablet, capsule, powder, syrup, liquid, suspension or injection.

5. The selective butyrylcholinesterase inhibitor having a general formula (I) or a pharmaceutically acceptable salt thereof according to claim 1, wherein the selective butyrylcholinesterase inhibitor is prepared by a preparation method that comprises:

taking 3-aminobenzoic acid as a starting material, forming a corresponding amide intermediate

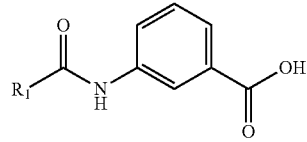

with an aromatic acid having a different ring system and different substituents, and then reacting with an intermediate

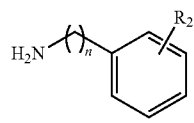

to prepare the selective butyrylcholinesterase inhibitor having general formula (I) or a pharmaceutically acceptable salt thereof;

wherein the reaction scheme is as follows:

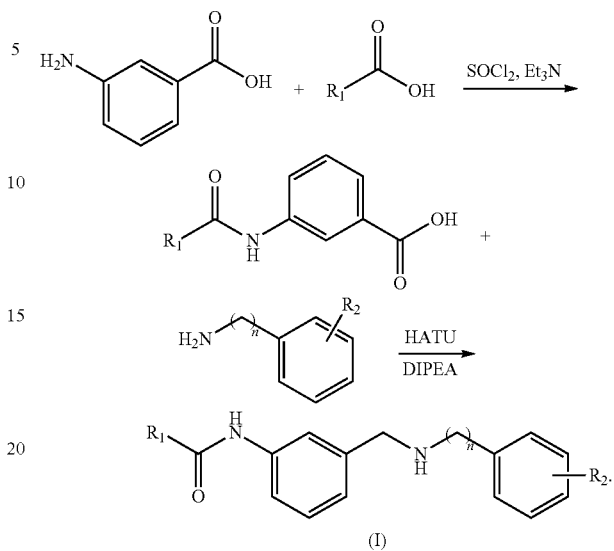

6. A method for treating Alzheimer's disease, comprising a step of administering the selective butyrylcholinesterase inhibitor of claim 1 to a subject in need for treating the Alzheimer's disease.

* * * * *